(12) United States Patent
Tepper et al.

(10) Patent No.: US 7,947,066 B2
(45) Date of Patent: May 24, 2011

(54) UNIVERSAL TRANSVERSE CONNECTOR DEVICE

(75) Inventors: Gil Tepper, Beverly Hills, CA (US); Kevin R. Strauss, Columbia, MD (US); Richard W. Woods, Catonsville, MD (US); Megan E. McMullen, Leesburg, VA (US); Mary P. Hamburger, Herndon, VA (US)

(73) Assignee: K2M, Inc., Leesburg, VA (US)

( * ) Notice: Subject to any disclaimer, the term of this patent is extended or adjusted under 35 U.S.C. 154(b) by 525 days.

(21) Appl. No.: 12/125,612

(22) Filed: May 22, 2008

(65) Prior Publication Data
US 2009/0043339 A1 Feb. 12, 2009

Related U.S. Application Data

(60) Provisional application No. 60/931,196, filed on May 22, 2007.

(51) Int. Cl.
*A61B 17/70* (2006.01)
(52) U.S. Cl. ........................................................ 606/278
(58) Field of Classification Search .................. 606/252, 606/253, 60, 258, 279, 86 A, 251, 914, 278, 606/254, 268, 250
See application file for complete search history.

(56) References Cited

U.S. PATENT DOCUMENTS

| | | | |
|---|---|---|---|
| 4,085,744 A | 4/1978 | Lewis et al. | |
| 5,010,879 A | 4/1991 | Moriya et al. | |
| 5,024,213 A | 6/1991 | Asher et al. | |
| 5,084,049 A | 1/1992 | Asher et al. | |
| 5,257,994 A | 11/1993 | Lin | |
| 5,275,600 A | 1/1994 | Allard et al. | |
| 5,312,405 A | 5/1994 | Korotko et al. | |
| 5,330,473 A * | 7/1994 | Howland | 606/250 |
| 5,330,474 A | 7/1994 | Lin | |
| 5,352,225 A | 10/1994 | Yuan et al. | |
| 5,395,370 A | 3/1995 | Müller et al. | |
| 5,439,463 A | 8/1995 | Lin | |
| 5,522,816 A | 6/1996 | Dinello et al. | |
| 5,569,246 A | 10/1996 | Ojima et al. | |
| 5,683,393 A | 11/1997 | Ralph | |
| 5,707,372 A | 1/1998 | Errico et al. | |
| 5,947,966 A * | 9/1999 | Drewry et al. | 606/252 |
| 5,980,523 A | 11/1999 | Jackson | |
| 5,989,251 A | 11/1999 | Nichols | |
| 6,096,039 A | 8/2000 | Stoltenberg et al. | |
| 6,110,173 A | 8/2000 | Thomas, Jr. | |
| 6,113,600 A | 9/2000 | Drummond et al. | |
| 6,136,003 A | 10/2000 | Hoeck et al. | |
| 6,171,311 B1 | 1/2001 | Richelsoph | |
| 6,217,578 B1 | 4/2001 | Crozel et al. | |
| 6,234,705 B1 | 5/2001 | Troxell | |

(Continued)

*Primary Examiner* — Pedro Philogene
(74) *Attorney, Agent, or Firm* — Carter, DeLuca, Farrell & Schmidt, LLP

(57) ABSTRACT

A connecting apparatus includes a first grasping member adapted to hold a first elongated member and a second grasping member adapted to hold a second elongated member. The second grasping member is operatively connected to the first grasping member so that the first and second grasping members are movable relative to each other. The apparatus further includes a first rotatable rod disposed in mechanical cooperation with the first grasping member, a second rotatable rod disposed in mechanical cooperation with the second grasping member, a first engaging member operatively connected to the first rotatable rod, and a second engaging member operatively connected to the second rotatable rod. The first engaging member is adapted to engage at least a portion of a first pedicle screw. The second engaging member is adapted to engage at least a portion of a second pedicle screw.

7 Claims, 32 Drawing Sheets

U.S. PATENT DOCUMENTS

| | | |
|---|---|---|
| 6,238,396 B1 | 5/2001 | Lombardo |
| 6,264,658 B1 | 7/2001 | Lee et al. |
| 6,283,967 B1 | 9/2001 | Troxell et al. |
| 6,306,137 B2 | 10/2001 | Troxell |
| 6,328,740 B1 | 12/2001 | Richelsoph |
| 6,328,741 B1 | 12/2001 | Richelsoph |
| 6,402,751 B1 | 6/2002 | Hoeck et al. |
| 6,554,832 B2 | 4/2003 | Shluzas |
| 6,602,253 B2 | 8/2003 | Richelsoph et al. |
| 6,616,668 B2 | 9/2003 | Altarac et al. |
| 6,736,817 B2 | 5/2004 | Troxell et al. |
| 6,872,208 B1 * | 3/2005 | McBride et al. ............ 606/86 A |
| 6,875,211 B2 | 4/2005 | Nichols et al. |
| 6,887,241 B1 | 5/2005 | McBride et al. |
| 6,958,066 B2 | 10/2005 | Richelsoph et al. |
| 6,991,632 B2 | 1/2006 | Ritland |
| 7,029,474 B2 * | 4/2006 | Richelsoph et al. .......... 606/252 |
| 7,137,986 B2 | 11/2006 | Troxell et al. |

* cited by examiner

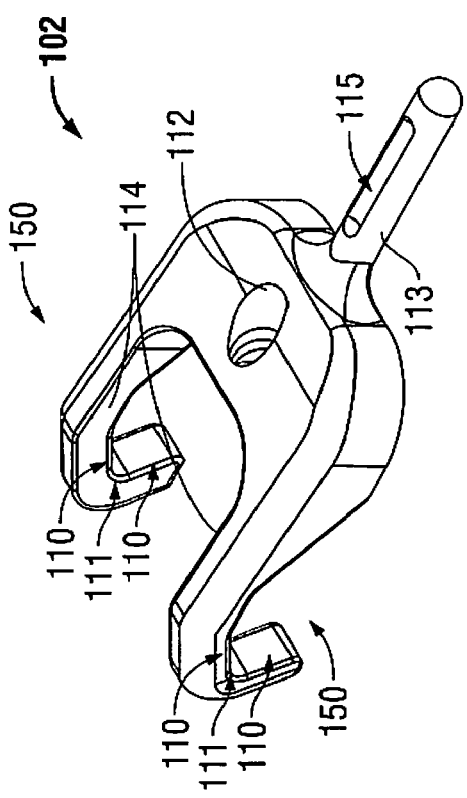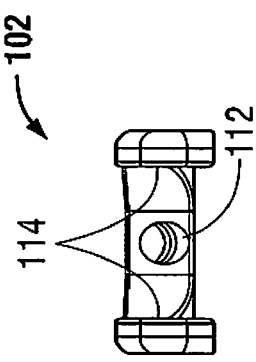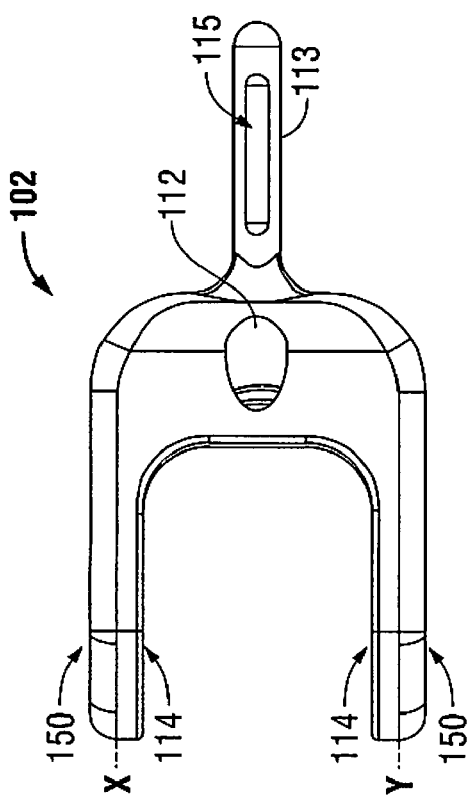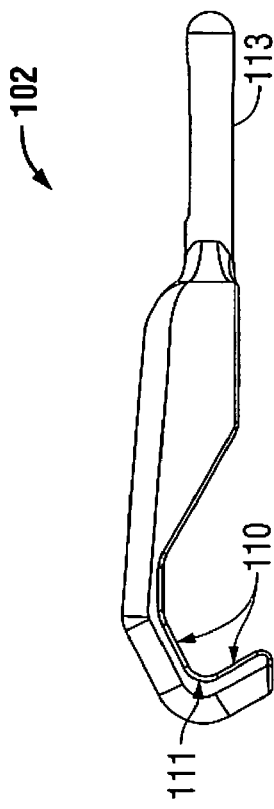
FIG. 3B
FIG. 3D
FIG. 3A
FIG. 3C

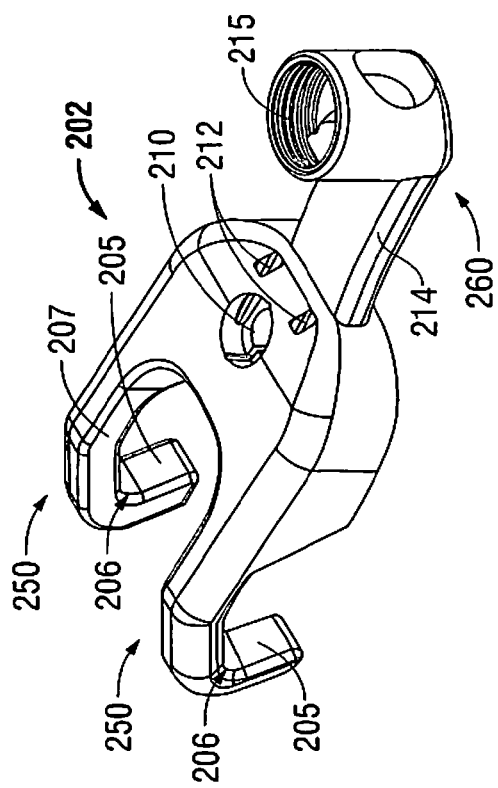
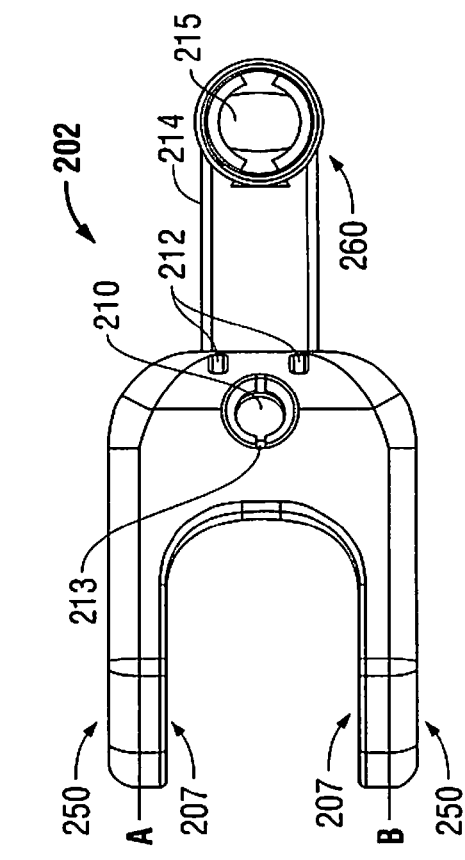
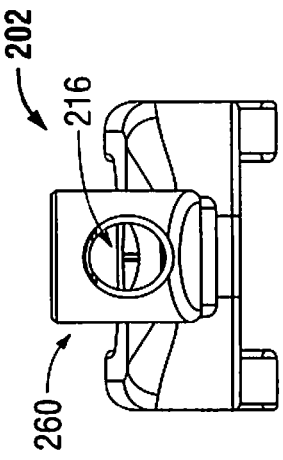
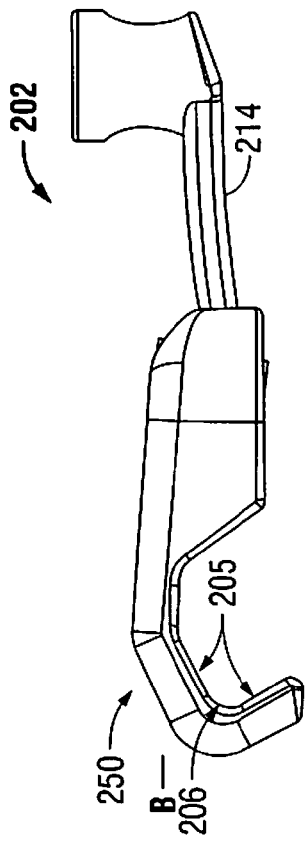
FIG. 14B
FIG. 14D
FIG. 14A
FIG. 14C

FIG. 15A  FIG. 15B

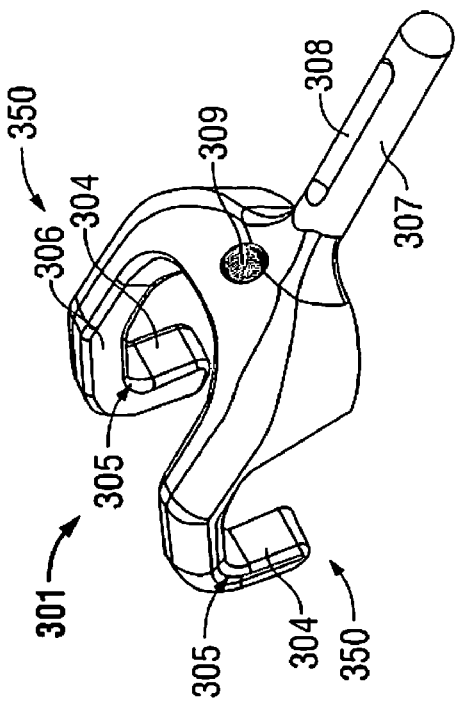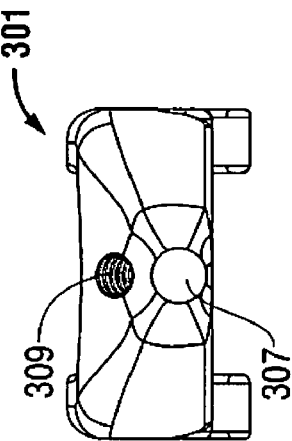
FIG. 18B
FIG. 18D
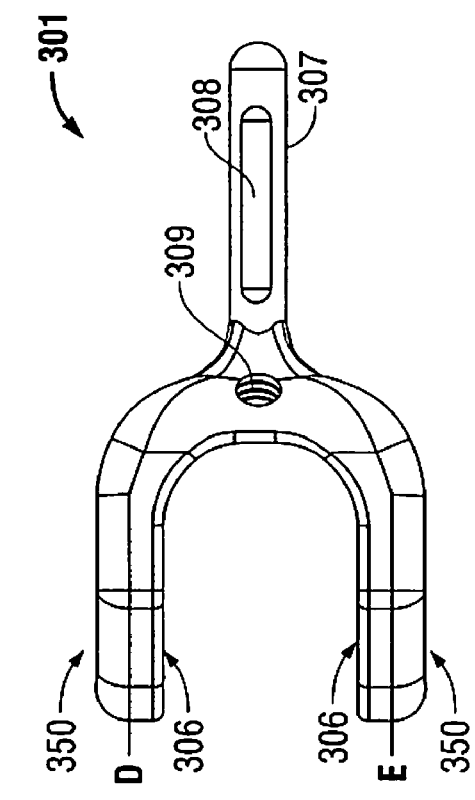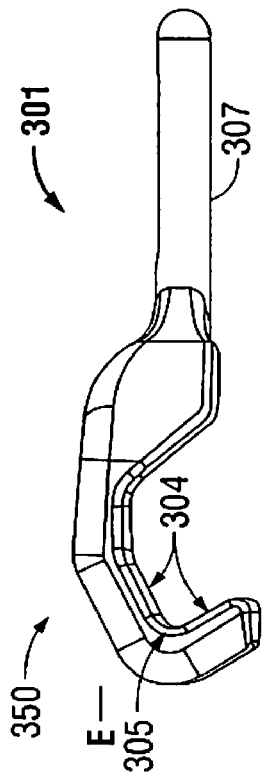
FIG. 18A
FIG. 18C

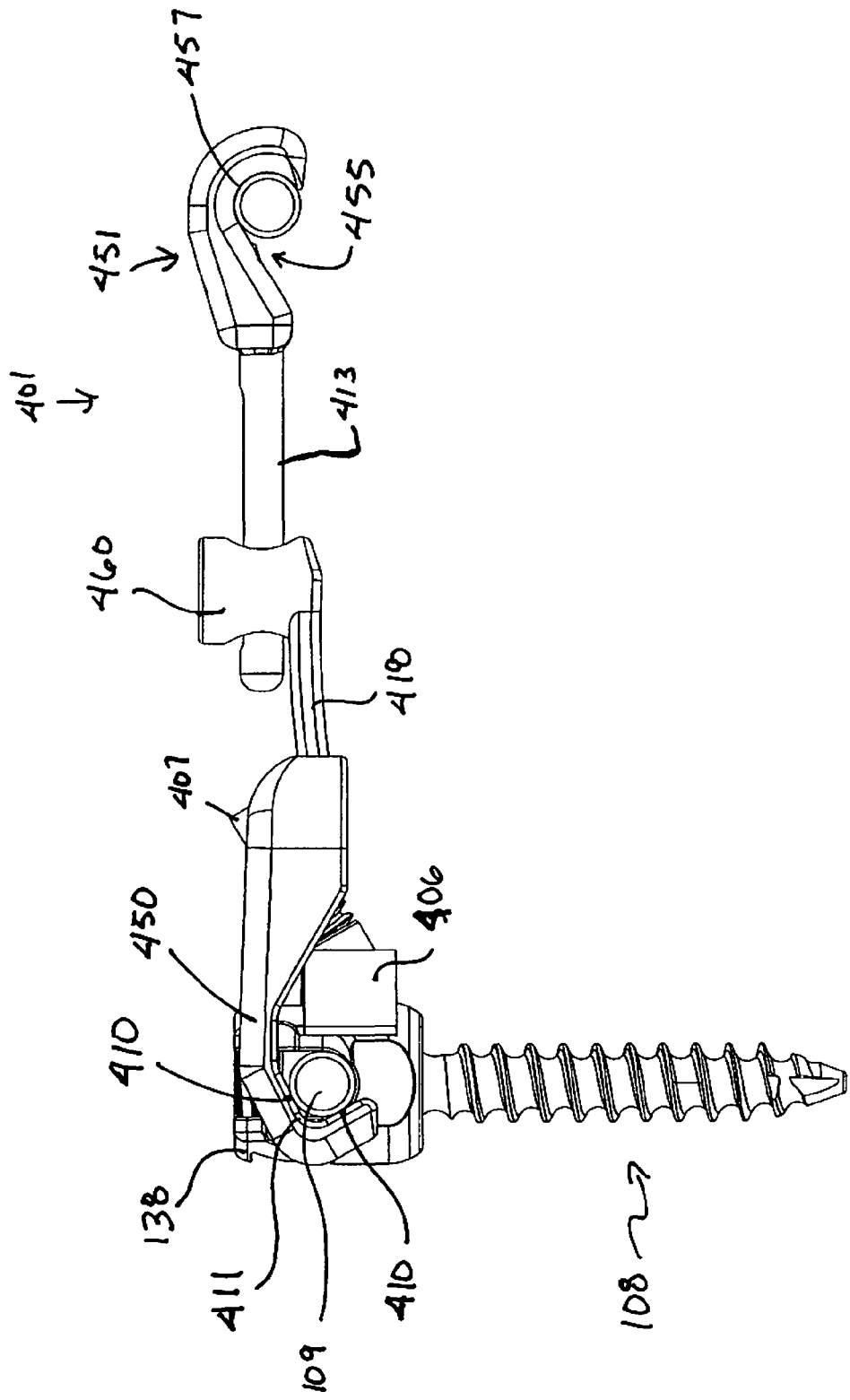

UNIVERSAL TRANSVERSE CONNECTOR DEVICE

CROSS-REFERENCE TO RELATED APPLICATION

This application claims priority to, and the benefit of, U.S. Provisional Patent Application Ser. No. 60/931,196, filed on May 22, 2007, the contents of which are hereby incorporated by reference in their entirety.

TECHNICAL FIELD

The present disclosure relates generally to a transverse connector device for use in orthopedic spine surgery. In particular, the present disclosure relates to a universal transverse connector device for coupling two pedicle screw supporting spinal fixation rods.

BACKGROUND

The spinal column is a complex system of bones and connective tissues that provide support for the human body and protection for the spinal cord and nerves. The adult spine is comprised of an upper and lower portion. The upper portion contains 24 discrete bones, which are subdivided into three areas including 7 cervical vertebrae, 12 thoracic vertebrae and 5 lumbar vertebrae. The lower portion is comprised of the sacral and coccygeal bones. The cylindrical shaped bones, called vertebral bodies, progressively increase in size from the upper portion downwards to the lower portion.

An intervertebral disc along with two posterior facet joints cushion and dampen the various translational and rotational forces exerted upon the spinal column. The intervertebral disc is a spacer located between two vertebral bodies. The facets provide stability to the posterior portion of adjacent vertebrae. The spinal cord is housed in the canal of the vertebral bodies. It is protected posteriorly by the lamina. The lamina is a curved surface with three main protrusions. Two transverse processes extend laterally from the lamina, while the spinous process extends caudally and posteriorly. The vertebral bodies and lamina are connected by a bone bridge called the pedicle.

The spine is a flexible structure capable of a large range of motion. There are various disorders, diseases and types of injury which restrict the range of motion of the spine or interfere with important elements of the nervous system. The problems include, but are not limited to, scoliosis, kyphosis, excessive lordosis, spondylolisthesis, slipped or ruptured discs, degenerative disc disease, vertebral body fracture, and tumors. Persons suffering from any of the above conditions typically experience extreme or debilitating pain and often times diminished nerve function.

Spinal fixation apparatuses are widely employed in surgical processes for correcting spinal injuries and diseases. These apparatuses commonly employ longitudinally link rods secured to coupling elements, which in turn are secured to the bone by spinal bone fixation fasteners such as pedicle screws, hooks, and others. The opposing pair of longitudinally linked rods is commonly disposed along the long axis of the spine and is held in position relative to one another by cross-connector devices, also know as transverse connectors or transverse bridge elements. This hardware is placed perpendicular to the rods and provides torsional stability and rigidity.

To meet the problem of securely connecting two opposing spinal rods, a requirement exists to provide a transverse connector device that can easily be rotated about all three axes and translated along the longitudinal axis of the transverse connector during the course of the surgical procedure and then be securely locked into the desired position. In addition, the transverse connector should have the ability to secure to rods of various diameters and should be adaptable to fit around a multitude of pedicle screw heads. Also, the device should be configured to provide a low profile with the smoothest possible contoured surfaces to avoid irritation of adjacent soft tissue and thus promote healing and comfort for the patient post operatively.

Commonly, transverse connectors are connected to opposing rods midway between two pedicle screws in adjacent vertebrae increasing rigidity, but also adding stress to the construct. The devices illustrated in U.S. Pat. No. 6,736,817 issued to Troxell et al., U.S. Pat. No. 6,217,578 issued to Crozet et al., and U.S. Pat. No. 7,029,474 issued to Richelsoph et al. encompass this trait. Many devices have been invented for the purpose of stabilizing the spine to increase the rigidity of the structure. These devices have the ability to connect to the rod of their designated system, but cannot adapt to other spinal systems, a desirable feature in the case of re-operation or adding on to existing implanted hardware.

Therefore, a need exists for a transverse connector that is secured to a rod at the pedicle screw and can be adaptable to multiple size rods and pedicle screws on the market, while not interfering with the normal anatomy.

SUMMARY

The present disclosure describes an apparatus for coupling surgical device. The presently disclosed apparatus includes a first grasping member adapted to hold a first elongated member and a second grasping member adapted to hold a second elongated member. The second grasping member is operatively connected to the first grasping member so that the first and second grasping members are movable relative to each other. The apparatus further includes a first rotatable rod disposed in mechanical cooperation with the first grasping member, a second rotatable rod disposed in mechanical cooperation with the second grasping member, a first engaging member operatively connected to the first rotatable rod, and a second engaging member operatively connected to the second rotatable rod. The first engaging member is adapted to engage at least a portion of a first pedicle screw and configured to translate upon rotation of the first rotatable rod. The second engaging member is adapted to engage at least a portion of a second pedicle screw and configured to translate upon rotation of the second rotatable rod.

Additionally, the present disclosure describes a connection system. This connection system includes a first spinal fixation rod, a second spinal fixation rod, a first pedicle screw having a first screw head, and a second pedicle screw having a second screw head. The first screw head defines a first saddle. The first spinal fixation rod is supported in the saddle. The second screw head defines a second saddle. The second spinal fixation rod is supported in the saddle. The connection system also includes a first grasping member holding the first spinal fixation rod and a second grasping member holding the second spinal fixation rod. The second grasping member is operatively connected to the first grasping member. Moreover, the connection system includes a first rotatable rod disposed in mechanical cooperation with the first grasping member, a second rotatable rod disposed in mechanical cooperation with the second grasping member, a first engaging member operatively connected to the first rotatable rod, and a second engaging member operatively connected to the second rotatable rod. The first engaging member is adapted to engage the first screw head and configured to translate upon rotation of the first rotatable rod. The second engaging member is adapted to engage the second screw head and configured to translate upon rotation of the second rotatable rod.

BRIEF DESCRIPTION OF DRAWINGS

Embodiments of the presently disclosed connector device are described herein with reference to the accompanying drawings, wherein:

FIG. 3A is a top view of an opposing rod grasping member of the universal connector device of FIG. 1A;

FIG. 3B is a perspective view of the rod grasping member of FIG. 3A;

FIG. 3C is a rear view of the rod grasping member of FIG. 3A;

FIG. 3D is a side view of the rod grasping member of FIG. 3A;

FIG. 14A is a top view of an opposing rod grasping member element of the universal connector device of FIG. 12A;

FIG. 14B is a perspective view of the rod grasping member of FIG. 14A;

FIG. 14C is a rear view of the rod grasping member of FIG. 14A;

FIG. 14D is a side view of the rod grasping member of FIG. 14A;

FIG. 15A is a top view of a locking pin of the universal connector device of FIG. 12A;

FIG. 15B is a perspective view of the locking pin of FIG. 15A;

FIG. 18A is top view of a rod grasping member of the universal connector device of FIG. 17A;

FIG. 18B is a perspective view of the rod grasping member of FIG. 18A;

FIG. 18C is a front view of the rod grasping member of FIG. 18A;

FIG. 18D is a side view of the rod grasping member of FIG. 18A;

FIG. 21C is a side view of the universal connector device of FIG. 21A.

DETAILED DESCRIPTION OF THE EMBODIMENTS

Figure 1A:
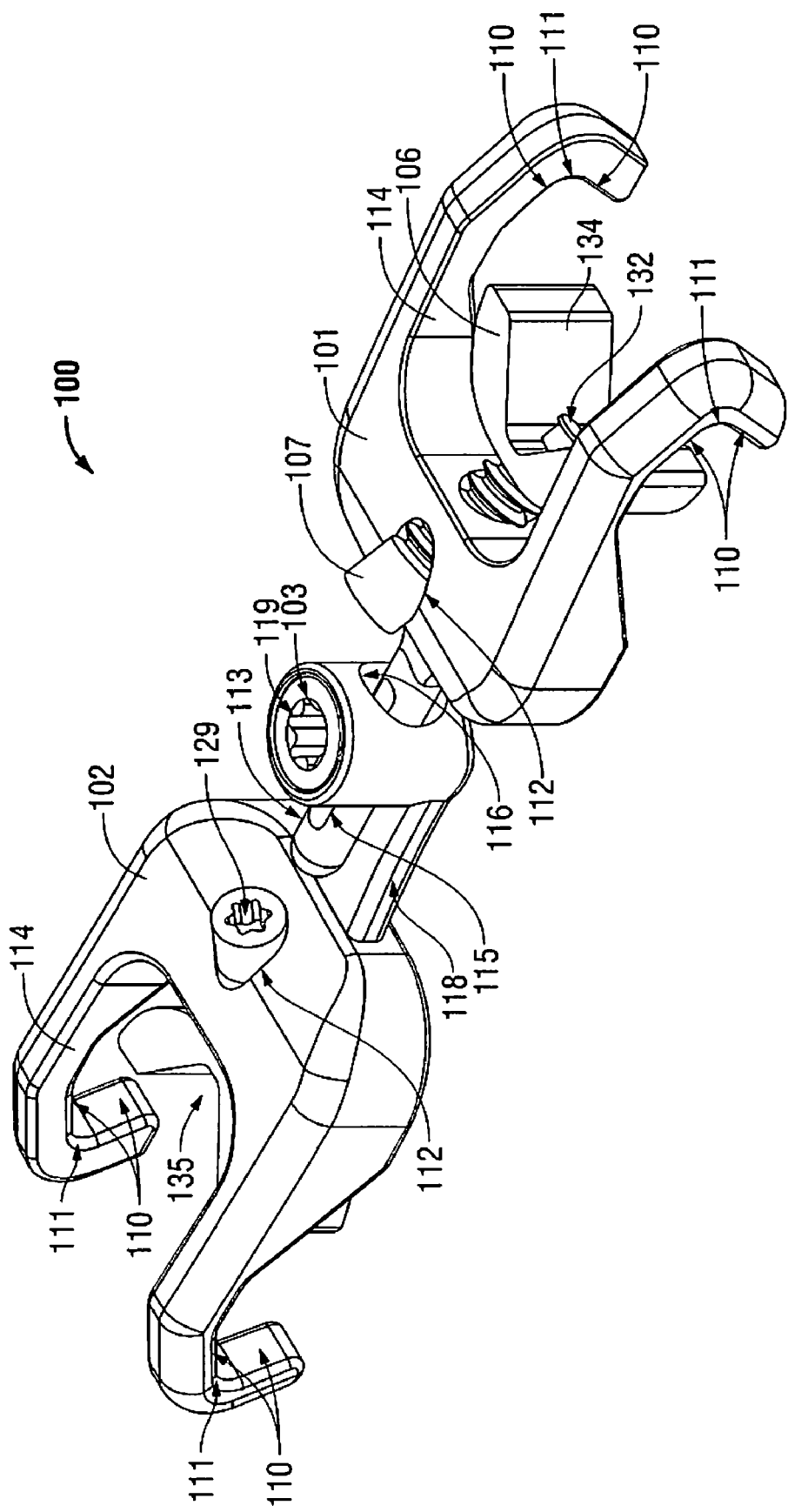
FIG. 1A is a perspective view of a universal connector device according to an embodiment of the present disclosure.
Figure 1B:
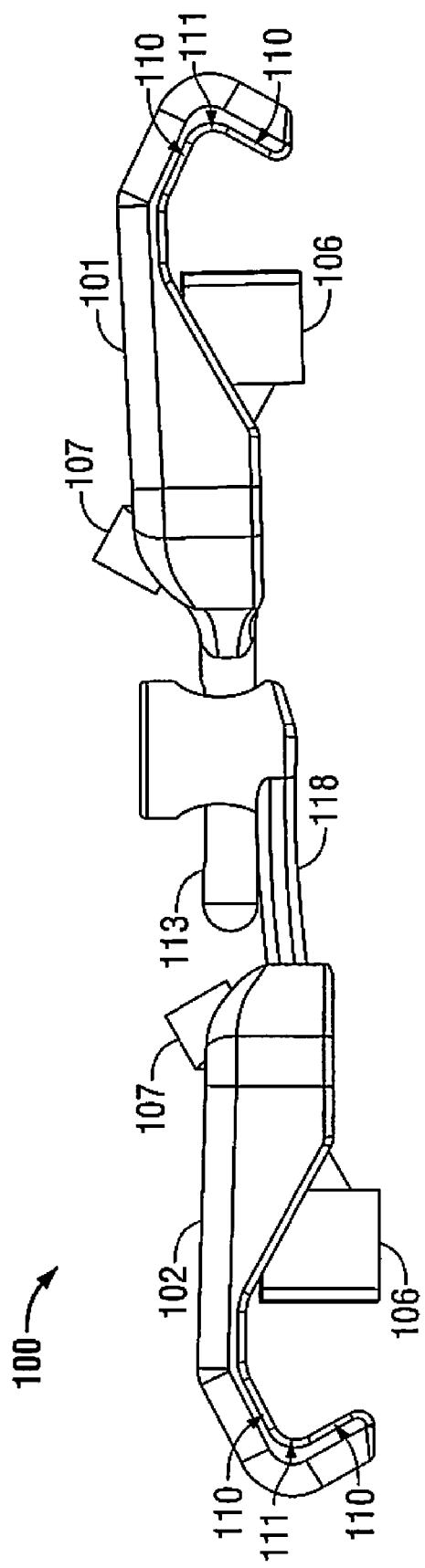
FIG. 1B is a front view of the universal connector device of FIG. 1A.
Figure 1C:
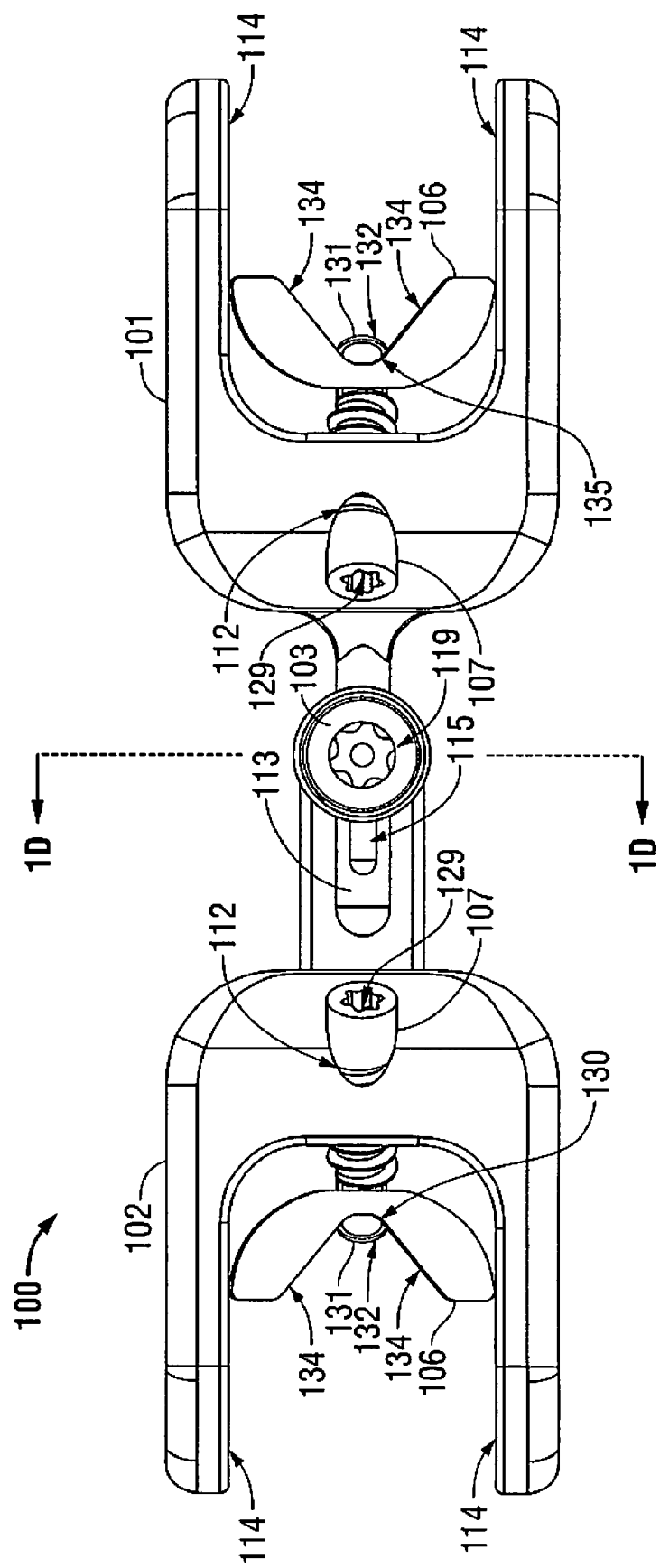
FIG. 1C is a top view of the universal connector device of FIG. 1A.

Embodiments of the presently disclosed universal connector device will now be described in detail with reference to the drawings, wherein like reference numerals identify similar or identical elements. In the drawings and description that follows, the term "proximal" will refer to the end of the universal connector device that is closest to the operator, while the term "distal" will refer to the end of the universal connector device that is farthest from the operator.

Figure 9A:
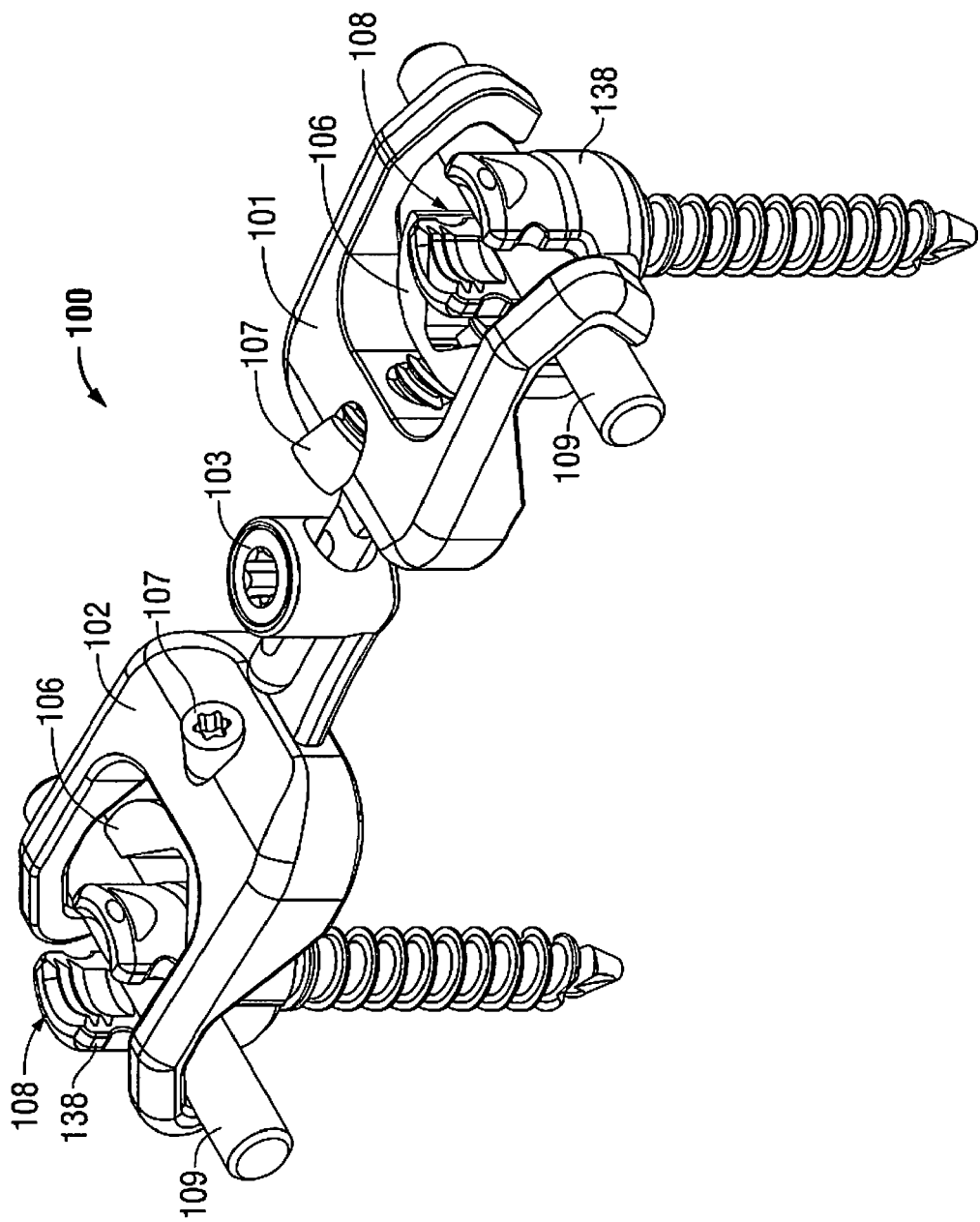
FIG. 9A is a perspective view of the universal connector device of FIG. 1A coupled to pedicle screws and spinal fixation rods.

FIGS. 1A-1D show an embodiment of the presently disclosed universal transverse connector device 100. Connector device 100 includes first and second rod grasping members or arms 101, 102 interconnected by a locking screw 103. Each rod grasping member 101, 102 contains a plate advancing member or screw 107 operatively coupled to a locking plate 106. Locking plates 106 are each adapted to receive and frictionally engage a screw head or tulip 138 of a pedicle screw 108, as shown in FIG. 9A. During operation, locking plates 106 move toward or away from the screw head 138 upon rotation of the corresponding plate advancing member 107.

Figure 10A:
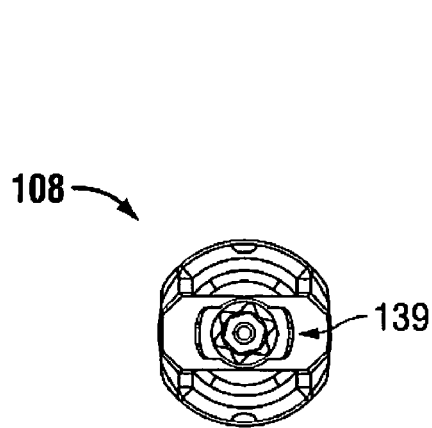
FIG. 10A is a top view of the polyaxial pedicle screw depicted in FIG. 9A.
Figure 10B:
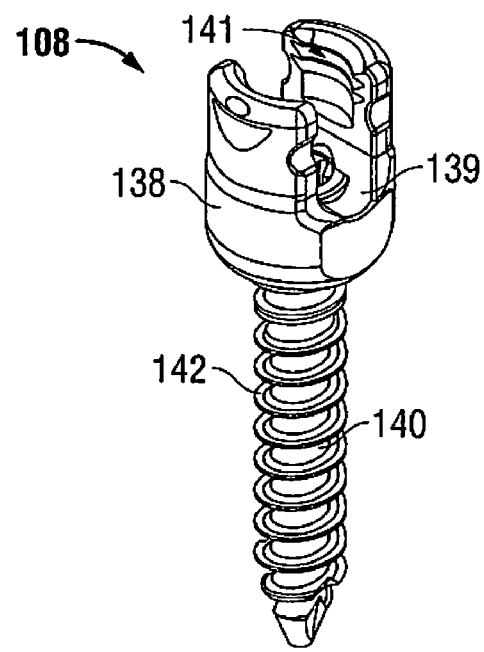
FIG. 10B is a perspective view of the polyaxial pedicle screw of FIG. 10A.
Figure 10C:
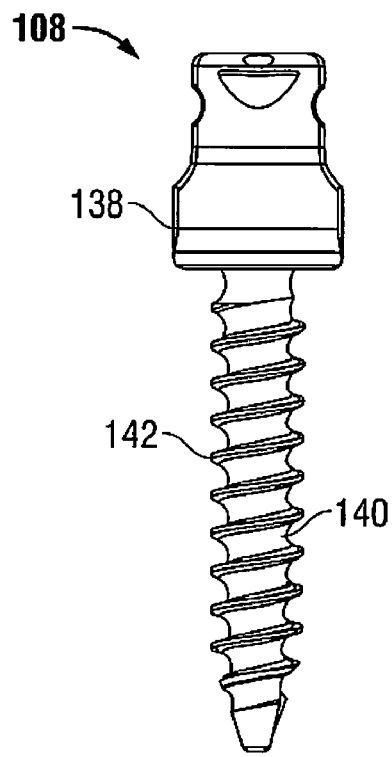
FIG. 10C is side view of the polyaxial pedicle screw of FIG. 10A.
Figure 10D:
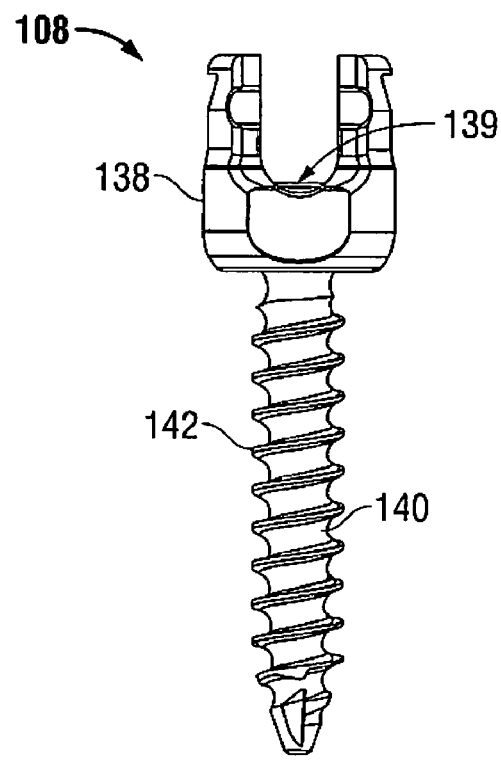
FIG. 10D is a front view of the polyaxial pedicle screw of FIG. 10A.

With reference to FIGS. 2A-2D, second rod grasping member 102 has a fork-like shape and includes a pair of rod engaging arms 150 defining a space 114 therebetween. Space 114 is dimensioned for surrounding the screw head 138 of a pedicle screw 108 (FIG. 10B). Each rod engaging arm 150 defines a longitudinal axes X, Y extending along at least a portion of its length and includes contacting surfaces 110 for engaging a spinal fixation rod 109, as depicted in FIG. 9A. Contacting surfaces 110 define an acute angle relative to the corresponding longitudinal axes X, Y. In one embodiment, contacting surfaces 110 include filleted portion with a radius 111 dimensioned to accommodate spinal fixation rod 109. Consequently, contacting surfaces 110 have a hook-like or generally C-shaped profile. Radius 111 may vary. For example, radius 111 may match the radius of the smallest commercially available spinal fixation rod 109. In addition to rod engaging arms 150, second rod grasping member 102 has a threaded hole 112 located at a center portion thereof. Threaded hole 112 is configured to receive plate advancing member or screw 107 and is oriented at an oblique angle with respect to longitudinal axes X, Y. Besides threaded hole 112, second rod grasping member 102 includes an extension member 118 protruding therefrom. Extension member 118 supports a post-receiving housing 160 in a proximal region thereof. Housing 160 includes an inner threaded area 117 and a portal or opening 116 adapted for receiving at least a portion of first grasping member 101. Inner threaded area 117 is configured to engage locking screw 103.

Referring now to FIGS. 3A-3D, first grasping member 101 is substantially similar to second grasping member 102. Like second grasping member 102, first grasping member 101 features a fork-like shape and includes a pair of rod engaging arms 150 defining a space 114 therebetween. Each rod engaging arm 150 has contacting surfaces 110 for engaging spinal fixation rod 109 (see FIG. 9A). Each contacting surface 110 defines an acute angle with respect to corresponding longitudinal axes X and Y. First grasping member 101 also includes a threaded hole 112 for receiving plate advancing member or screw 107. Threaded hole 112 is oriented at an oblique angle relative to longitudinal axes X and Y. Unlike first grasping member 102, first grasping member 101 includes an extension member 113 having alignment slot 115 for slidably receiving an alignment post 104 (see FIGS. 6A-6D). When first and second grasping members 101, 102 are connected to each other, alignment post 104 guides the relative movement of first and second grasping members 101, 102 with respect to one another. Alignment post 104 and alignment post 115 jointly hinder disconnection of first and second grasping members 101, 102 and cooperatively maintain a minimum and maximum relative distance between first and second grasping members 101, 102. Despite the latter, alignment post 104 is optional. When first and second grasping members 101, 102 are coupled without alignment post 104, first and second grasping members 101, 102 can rotate with respect to each other. As mentioned above, locking screw 103 connects and locks first and second grasping members 101, 102 relative to each other.

Figure 1D:
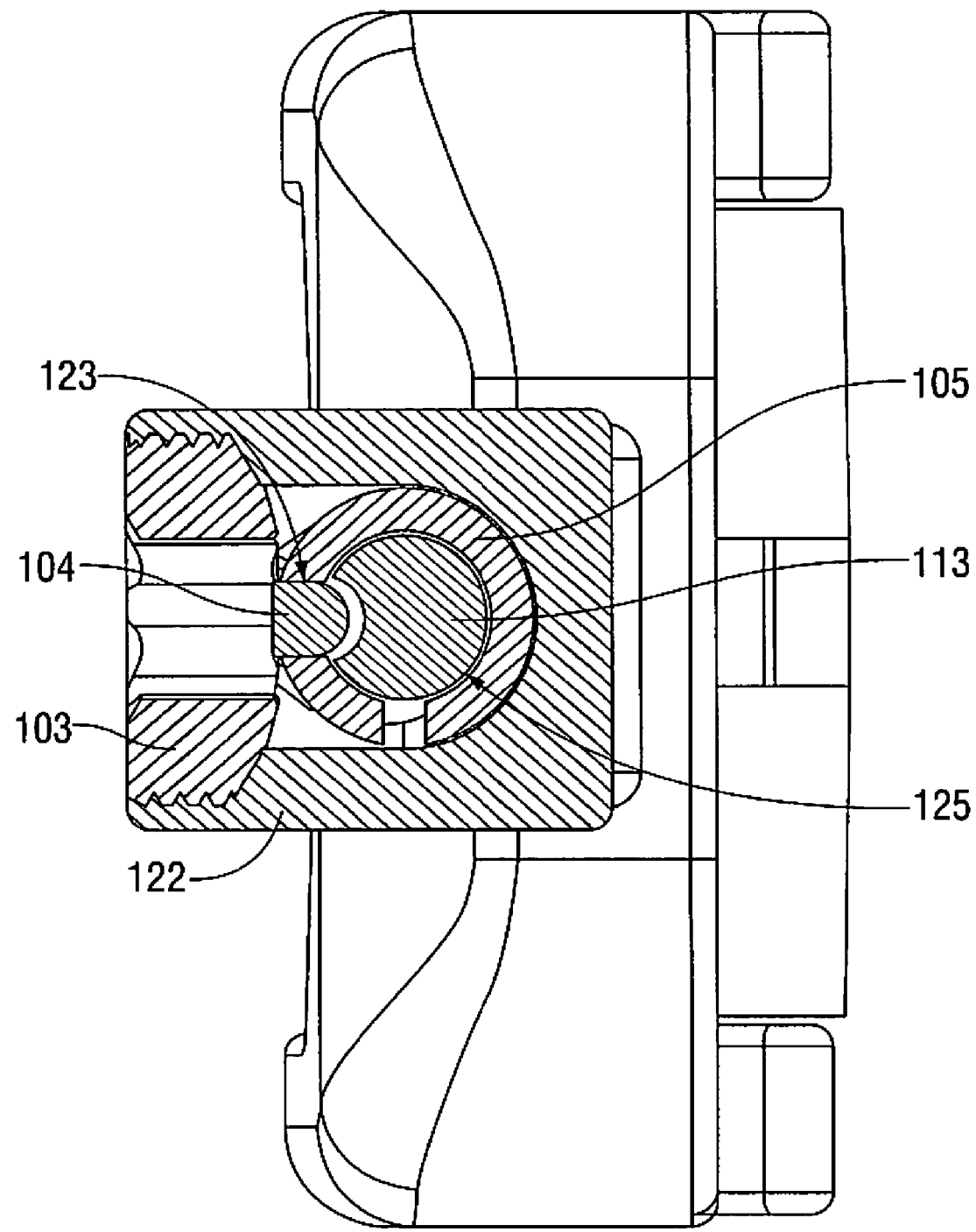
FIG. 1D is a cross-sectional side view of the connector device of FIG. 1A, taken along section line A-A of FIG. 1C.
Figure 2B:
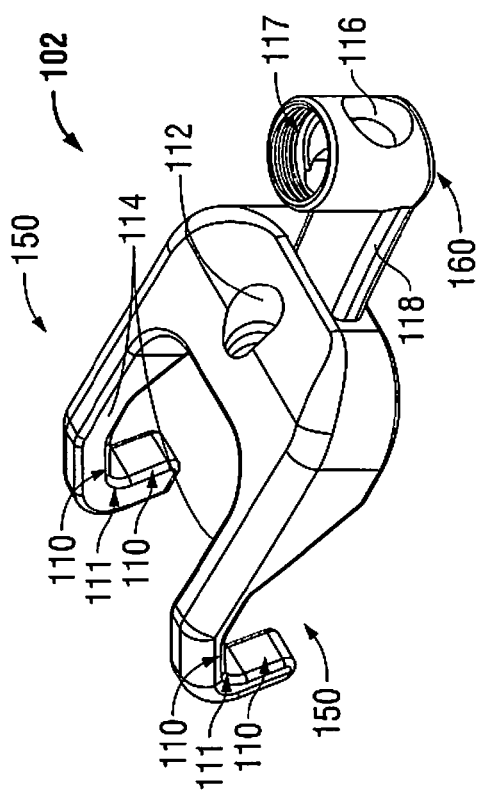
FIG. 2B is a perspective view of the rod grasping member of FIG. 2A.
Figure 2D:
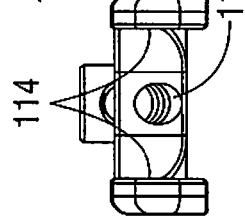
FIG. 2D is a side view of the rod grasping member of FIG. 2A.
Figure 2A:
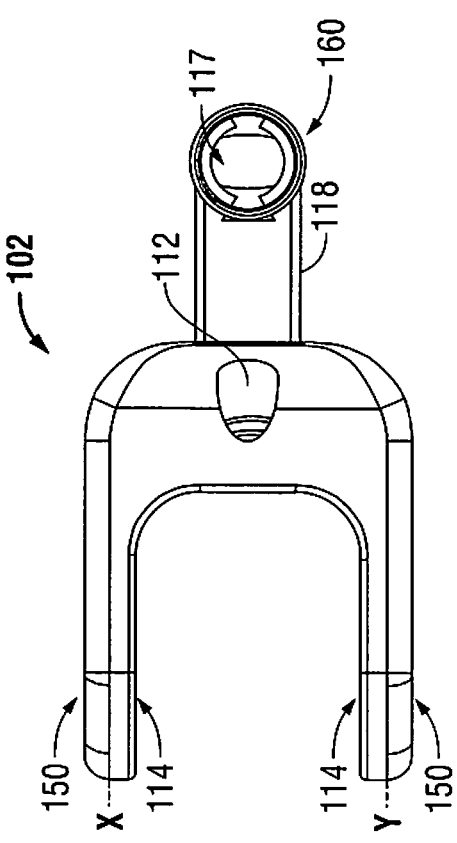
FIG. 2A is a top view of a rod grasping member of the universal connector device of FIG. 1A.
Figure 2C:
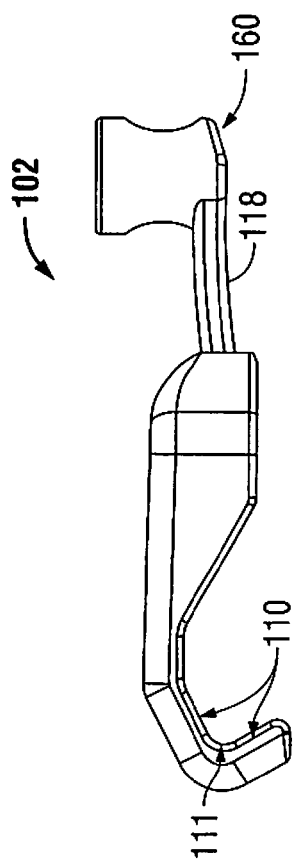
FIG. 2C is a front view of the rod grasping member of FIG. 2A.
Figure 4A:
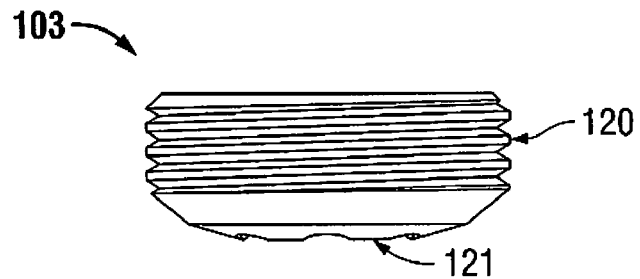
FIG. 4A is a front view of a locking screw of the universal connector device of FIG. 1.
Figure 4B:
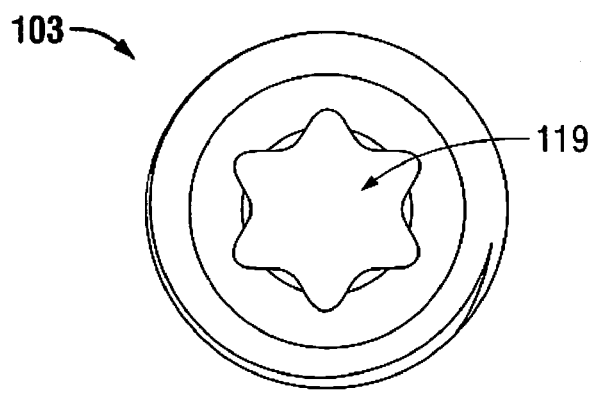
FIG. 4B is a top view of the locking screw of FIG. 4A.
Figure 4C:
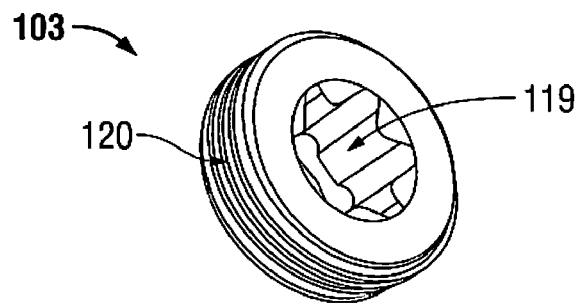
FIG. 4C is a perspective view of the locking screw of FIG. 4A.
Figure 5A:
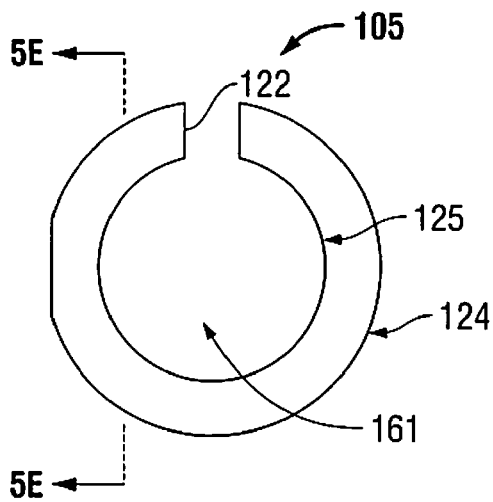
FIG. 5A is a top view of a slip ring of the universal connector device of FIG. 1A.
Figure 5B:
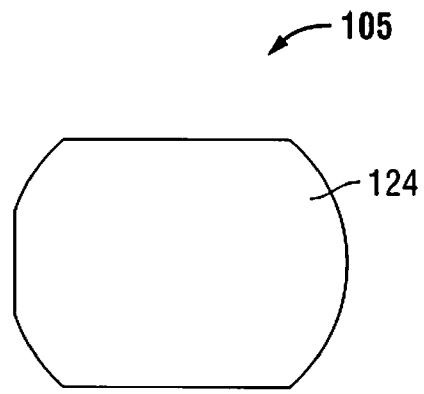
FIG. 5B is a front view of the slip ring of FIG. 5A.
Figure 5C:
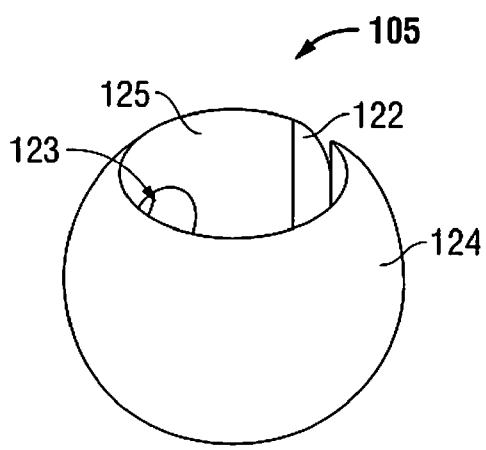
FIG. 5C is a perspective view of the slip ring of FIG. 5A.
Figure 5D:
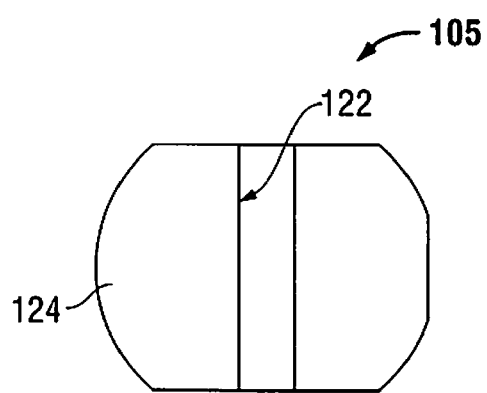
FIG. 5D is a rear view of the slip ring of FIG. 5A.
Figure 5E:
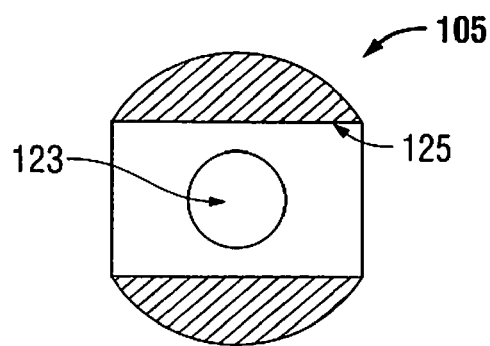
FIG. 5E is a cross-sectional side view of the slip ring of FIG. 5A, taken along section line B-B of FIG. 5A.
Figure 6A:
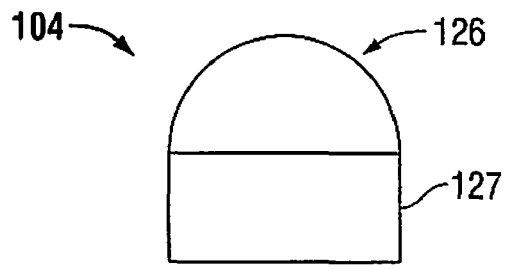
FIG. 6A is side view of an alignment post of the universal connector device of FIG. 1A.
Figure 6B:
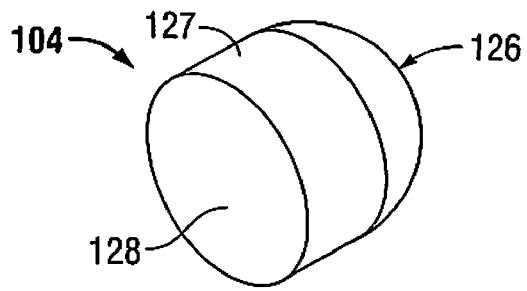
FIG. 6B is a perspective view of the alignment post of FIG. 6A.
Figure 6C:
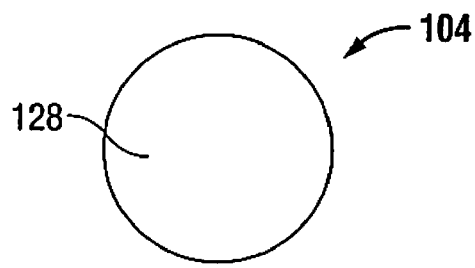
FIG. 6C is a bottom view of the alignment post of FIG. 6A.
Figure 6D:
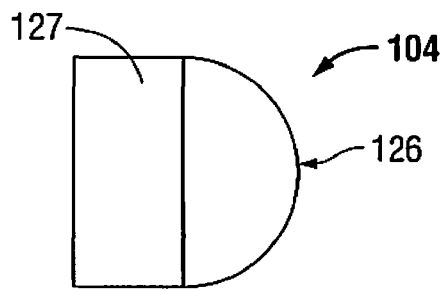
FIG. 6D is a side view of the alignment post of FIG. 6A.
Figure 7A:
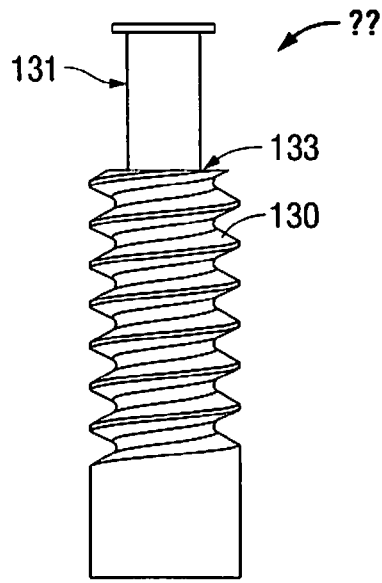
FIG. 7A is a front view of a plate advancing screw of the universal connector device of FIG. 1A.
Figure 7B:
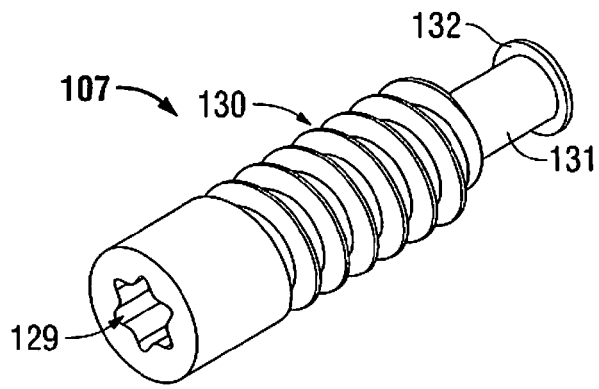
FIG. 7B is a perspective view of the plate advancing screw of FIG. 7A.
Figure 7C:
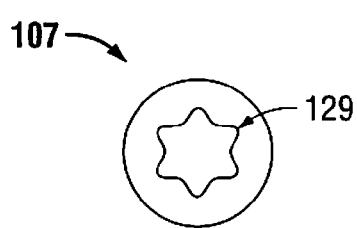
FIG. 7C is a side view of the plate advancing screw of FIG. 7A.
Figure 7D:
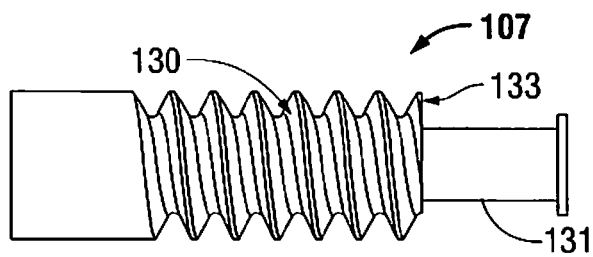
FIG. 7D is a rear view of the plate advancing screw of FIG. 7A.

Referring to FIGS. 4A-4C, locking screw 103 contains an external thread 120 configured to engage inner threaded area 117 of housing 160. During assembly, the operator can lock first grasping member 101 to second grasping member 102 by placing locking screw 103 within housing 160 and then rotating locking screw 103. As locking screw 103 rotates, external thread 120 engages inner threaded area 117, thus fixing the position of first grasping member 101 with respect to second grasping member 102. In addition to external thread 120, locking screw 103 includes a hexalobular drive receiver or socket 119 defining an undulated inner periphery. Opening 119 extends through locking screw 103 and is adapted to receive alignment post 104 (see FIGS. 6A-6D). The undulated inner periphery of opening 119 facilitates engagement of locking screw 130 with a hexalobular drive. It is envisioned that opening 119 may have other shapes or configurations suitable to receive and engage other kinds of drivers or instruments. Locking screw 103 further includes a substantially convex bottom surface 121 that contacts at least a portion of a slip ring 105 when connector device 100 is assembled, as shown in FIG. 1D.

As best seen in FIGS. 5A-5D, slip ring 105 has a substantially spherical shape and, in conjunction with locking screw 103 (see FIG. 1D), helps to fix the position of second grasping member 102 relative to first grasping member 101. Slip ring 105 includes an inner surface 125 and an outer surface 124. Inner surface 125 defines a bore 161 adapted to receive an extension member 113 of first grasping member 101, as shown in FIG. 1D. Aside from bore 161, slip ring 105 also includes a gap 122 extending along its length. During operation, gap 122 allows slip ring 105 to compress as locking screw 103 (see FIG. 1D) is screwed into housing 160. While locking screw 103 moves toward slip ring 105 in a response to rotation by a user, locking screw 103 compresses slip ring 105 and, in turn, the size of gap 122 decreases. The compressive force exerted on slip ring 105 transfers to extension member 113 of first grasping member 101 and hinders rotation and translation of first grasping member 101 relative to second grasping member 102. In addition to gap 122, slip ring 105 contains an alignment post hole 123 adapted to receive alignment post 104, as depicted in FIG. 1D.

Referring to FIGS. 6A-6D, alignment post 104 has a hemispherical region 126 configured for slidable reception within alignment slot 115 of extension member 113 and a cylindrical region 127 adapted for reception within alignment post hole 123 of slip ring 105. Cylindrical portion 126 contains a flat surface 128. When first and second grasping members 101, 102 are connected to each other, at least a portion of hemispherical region 126 is located within alignment slot 115 and at least a portion of cylindrical region 127 is positioned within alignment post hole 123, as shown in FIG. 1D.

With reference to FIGS. 7A-7D, connector device 100 includes a pair of plate advancing members or screws 107. Each plate advancing member 107 assists in the movement of the corresponding locking plates 106 toward or away of the screw head 138 of a pedicle screw 108, as seen in FIG. 9A. Plate advancing members 107 each include an external helical thread 130, a tubular section 131 attached to the distal end 133 of the external helical thread 130, and a hexalobular drive receiver or socket 129 positioned at a proximal end thereof. Hexalobular drive receiver 129 is configured to receive a hexalobular drive or any other suitable driving device. Although the drawings depict a plate advancing member 107 with a hexalobular drive receiver or socket 129, opening 129 may have other configurations suitable to engage with other driving devices. The cross-section or diameter of tubular section 131 is smaller than the remaining cross-section of plate advancing member 107. Tubular section 131 also has an end cap or flange 132 at a distal end thereof. When plate advancing member 107 is attached to locking plate 106, tubular section 131 supports locking plate 106 (see FIG. 8A). While the configuration of tubular section 131 allows locking plate 106 to rotate freely thereabout, end cap or flange 132 inhibits detachment of locking plate 106 from plate advancing member 107. During operation, a user engages a driving device to hexalobular drive receiver 129 and rotates the driving device to rotate plate advancing member 107. The rotation of plate advancing member 107 causes the translation of plate advancing member 107 to rotate away or toward the screw head of a pedicle screw 108. (See FIG. 9A). The translation of plate advancing member 107 causes in turn the translation of locking plate 106.

Figure 8A:
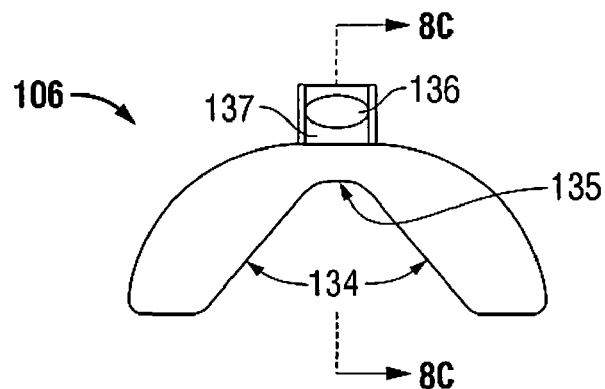
FIG. 8A is a top view of a locking plate of the universal connector device of FIG. 1A.
Figure 8B:
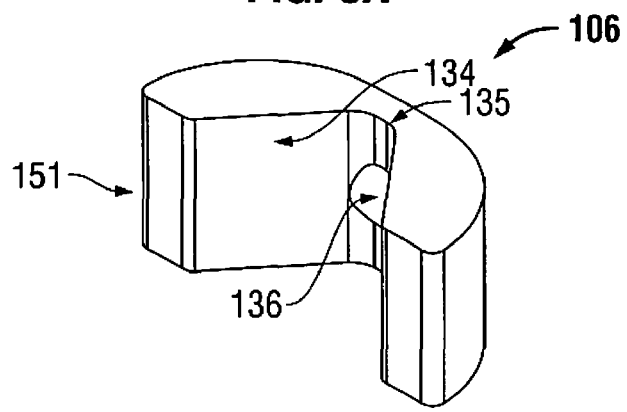
FIG. 8B is a perspective view of the locking plate of FIG. 5A.
Figure 8C:
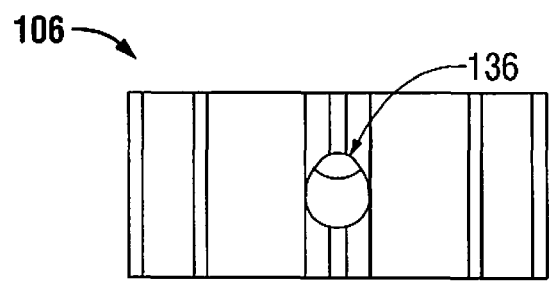
FIG. 8C is a front view of the locking plate of FIG. 8A.
Figure 8D:
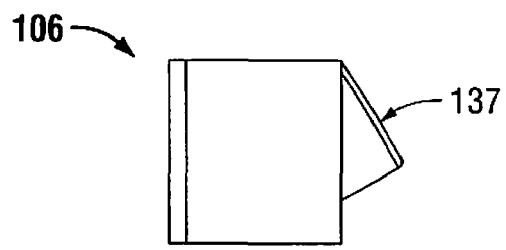
FIG. 8D is side view of the locking plate of FIG. 8A.

With reference to FIGS. 8A-8C, locking plate 106 has a fork-like shape and includes a pair of engaging protrusions 151 extending therefrom and a connecting portion 135 interconnecting engaging protrusions 151. Connecting portion 135 is oriented substantially perpendicular to a central longitudinal axis C. Each engaging protrusion 151 defines a contacting surface 134 defining an oblique angle relative to central axis C. In use, contacting surfaces 134 frictionally engage the screw head of a pedicle screw 108. (See FIG. 9A). Locking plate 106 further includes an angled portion 137 oriented at an oblique angle with respect to central longitudinal axis C. The angle defined by angled portion 137 relative to central longitudinal axis C is substantially similar to the angle defined by threaded hole 112 (see FIG. 1A) relative to longitudinal axes X and Y. A thru hole 136 extends from angled portion 137 to central portion 135 and is configured to receive at least a portion of plate advancing member 107. Moreover, thru hole 136 defines an angle relative to central longitudinal axis C that is substantially similar to the angle defined by threaded hole 112 (see FIG. 1A) relative to longitudinal axes X and Y.

Figure 9B:
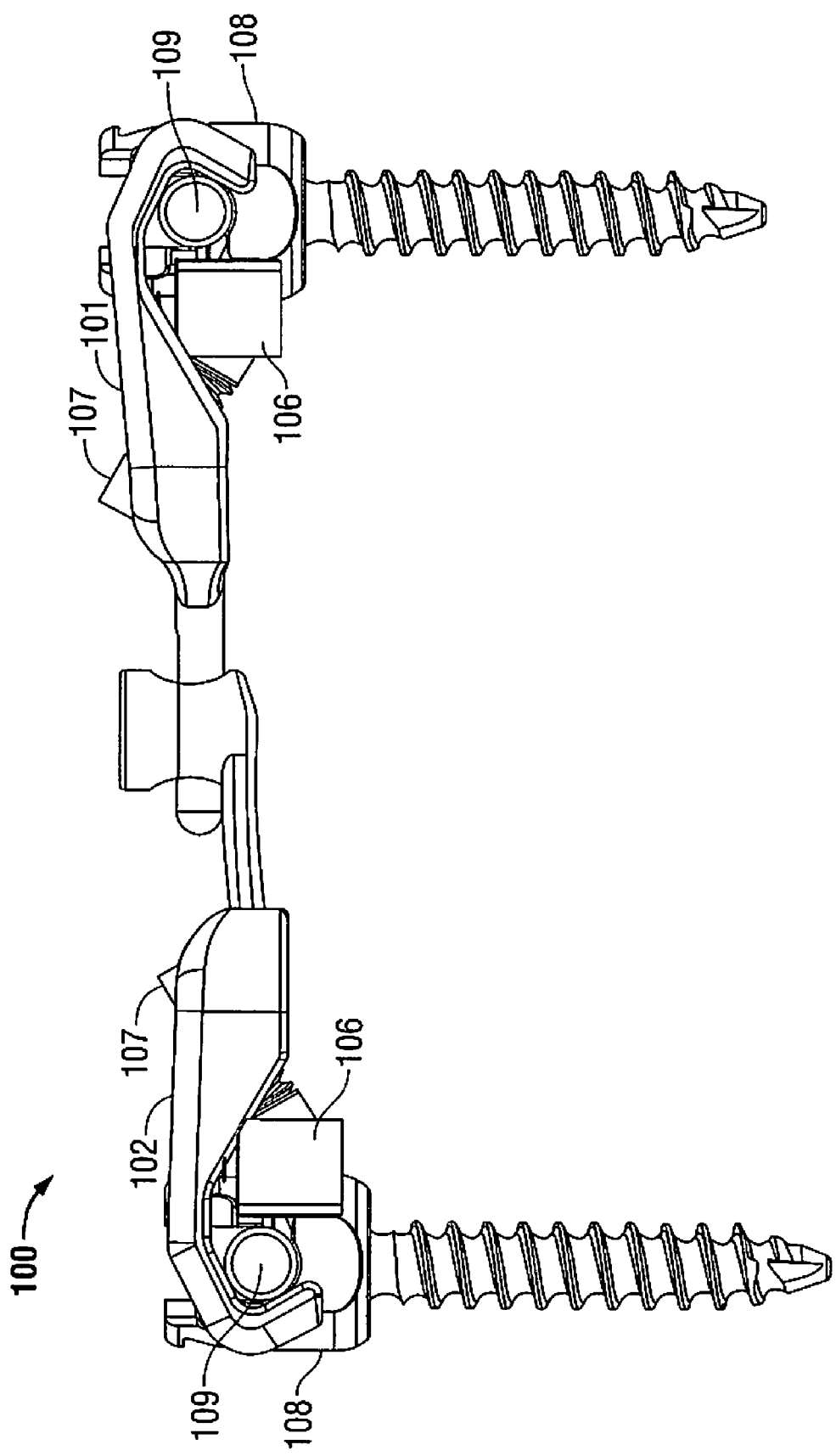
FIG. 9B is a front view of the universal connector device, the polyaxial pedicle screws, and the spinal fixation rods shown in FIG. 9A.
Figure 9C:
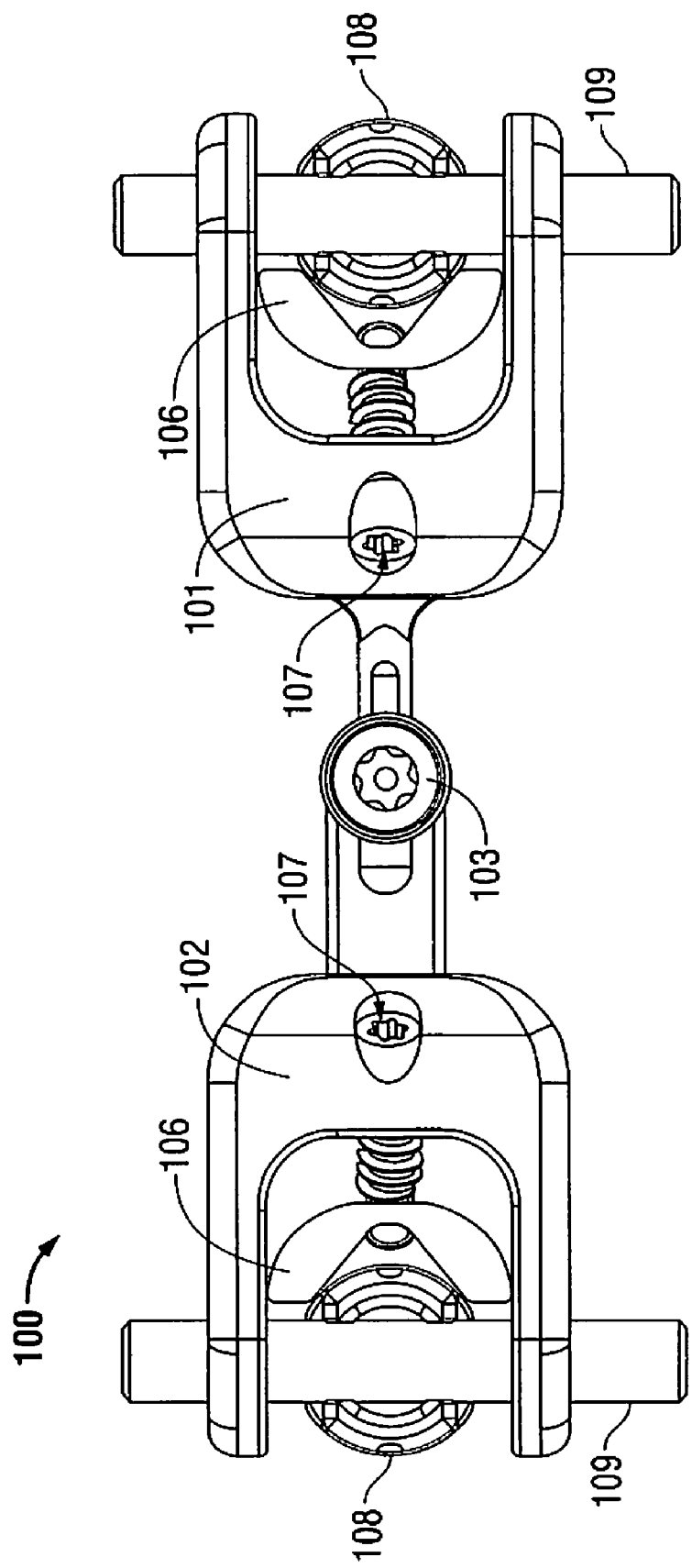
FIG. 9C is a top view of the universal connector device, the polyaxial pedicle screws, and the spinal fixation rods shown in FIG. 9A.

In use, universal transverse connector 100 holds and supports two pedicle screws 108 and two spinal fixation rods 109, as shown in FIGS. 9A-9C. Even though the drawings show specific kinds of pedicle screws 108 and spinal fixation rods 109, universal transverse connector 100 may support any kind of suitable pedicle screws and spinal fixation rods.

As seen in FIGS. 10A-10D, the presently disclosed polyaxial pedicle screw 108 includes a screw head 138 pivotally coupled to a shank 140. Screw head 138 includes a saddle 139 adapted to receive spinal fixation rod 103 and helical threads 141 formed on an inner surface thereof. Helical threads 141 are configured for threadably engaging a corresponding thread on a locking element (not shown). The locking element may be a setscrew or any other suitable threaded apparatus, instrument, or device. Shank 140 also has a helical thread 142 formed on an outer surface of shank 140. Helical thread 142 is configured to engage a vertebral body.

Instead of the presently disclosed polyaxial pedicle screw 108, universal transverse connector 100, or any of the other embodiment described below, can hold posterior pedicle screws having a taper lock. U.S. Provisional Patent Application Ser. No. 61/000,071, filed on Oct. 23, 2007, the entire contents of which are herein incorporated by reference, describes in detail the structure and operation of the posterior pedicle screws. Generally, the posterior pedicle screw construct includes a pedicle screw, a coupling, and a collet. The coupling and the collet are fastened with a pin that prevents relative rotation between the collet and the coupling. The pedicle screw is capable of rotating relative to the collet and coupling assembly. In addition, the posterior pedicle screw is capable of angular movement relative to the collet and the coupling. The inner surfaces of the collet and the coupling include a beveled or chamfered lip that reduces the interference with the pedicle screw, thereby increasing the angular range of motion. The range of angular movement is from about 0° to about 90°. In another embodiment, the range of angular movement is from about 0° to about 95°.

Figure 11A:
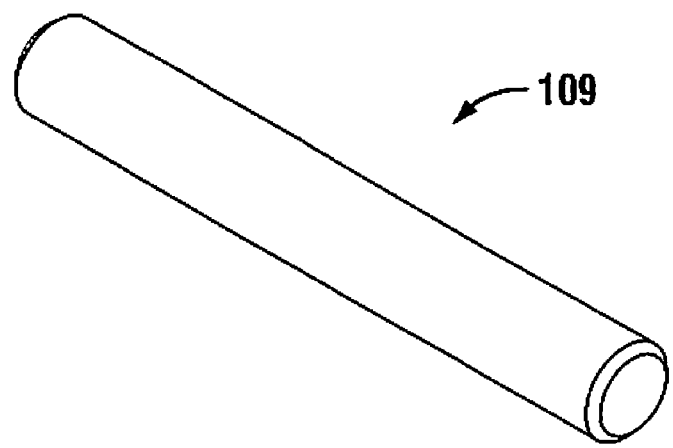
FIG. 11A is a perspective view of a spinal fixation rod shown in FIG. 9A.
Figure 11B:
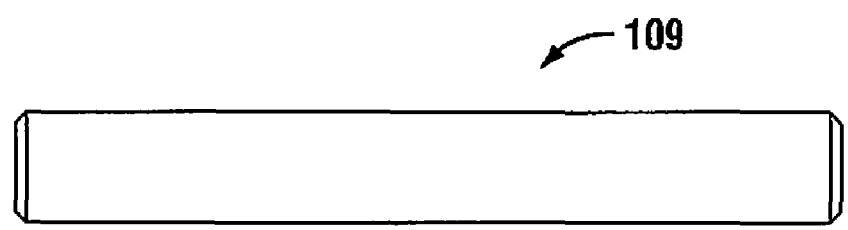
FIG. 11B is a side view of the spinal fixation rod of FIG. 11A.
Figure 11C:
FIG. 11C is a front view of the spinal fixation rod of FIG. 11A.

With reference to FIGS. 11A-11C, spinal fixation rod 109 facilitates stabilization of the spine when coupled to a pedicle screw 108 (see FIG. 10A) attached to a vertebral body. Spinal fixation rod 109 has a cylindrical shape and may be made of any suitable biocompatible material. For example, spinal fixation rod 109 may be made of titanium, titanium alloy, nickel titanium alloy, stainless steel, cobalt chromium alloy, or any other suitable material. During use, once polyaxial pedicle screws 108 are attached to a vertebral body, spinal fixation rod 109 facilitates the stabilization of those vertebral bodies.

Referring back to FIGS. 9A-9C, a physician may employ universal transverse connector 100 in conjunction with pedicle screws 108 and spinal fixation rods 109 to stabilize adjacent vertebral bodies. To stabilize vertebral bodies with universal transverse connector 100, the user initially inserts pedicle screws 108 into vertebral bodies by employing any surgical method known in the art and places a spinal fixation rod 109 in each saddle 139 of pedicle screws 108. The user then adjusts the relative position of first and second rod grasping members 101, 102 by translating extension members 113, 118 relative to each other. As extension members 113, 118 move relative to each other, extension member 113 of first rod grasping member 101 passes through opening 116 of housing 160 (see FIG. 2B). While extension member 113 translates through opening 116, alignment post 104 (see FIG. 1D) slides along alignment slot 115 of extension member 113. After placing first and second rod grasping members 101, 102 in the desired relative position, the user locks first and second rod grasping members 101, 102 in place. To fix the relative position of first and second rod grasping member 101, 102, the operator rotates locking screw 103 with a hexalobular drive, or any other suitable device, to move locking screw 103 toward extension member 113. Translating locking screw 103 toward extension member 113 compresses slip ring 105 and decreases the size of gap 122. When locking screw 103 compresses slip ring 105, slip ring 105 in turn compresses extension member 113, thereby hindering rotation and translation of extension member 113 (see FIG. 1D).

Once first and second rod grasping members 101, 102 have been locked in place, the user places rod engaging arm 150 of universal transverse connector 100 on top of spinal fixation rods 109. Afterwards, the user rotates plate advancing members 107 to move advance locking plates 106 toward screw heads 138 of pedicle screws 108. The continued rotation of plate advancing members 107 pushes screw heads 138, along with spinal fixation rods 109, toward contacting surfaces 110. The user keeps rotating plate advancing members 107 until spinal fixation rods 109 firmly engage contacting surfaces 110 of first and second rod grasping members 101, 102, thereby locking universal transverse connector to pedicle screws 108.

Figure 12A:
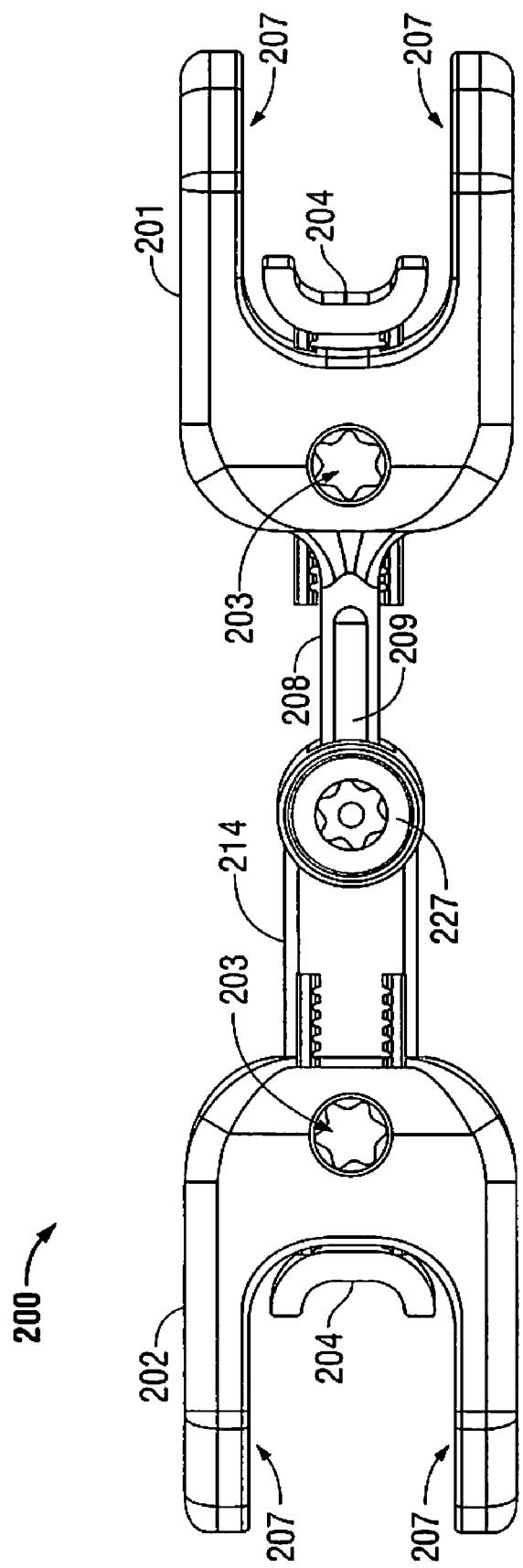
FIG. 12A is a top view of a universal connector device according to another embodiment of the present disclosure.
Figure 12B:
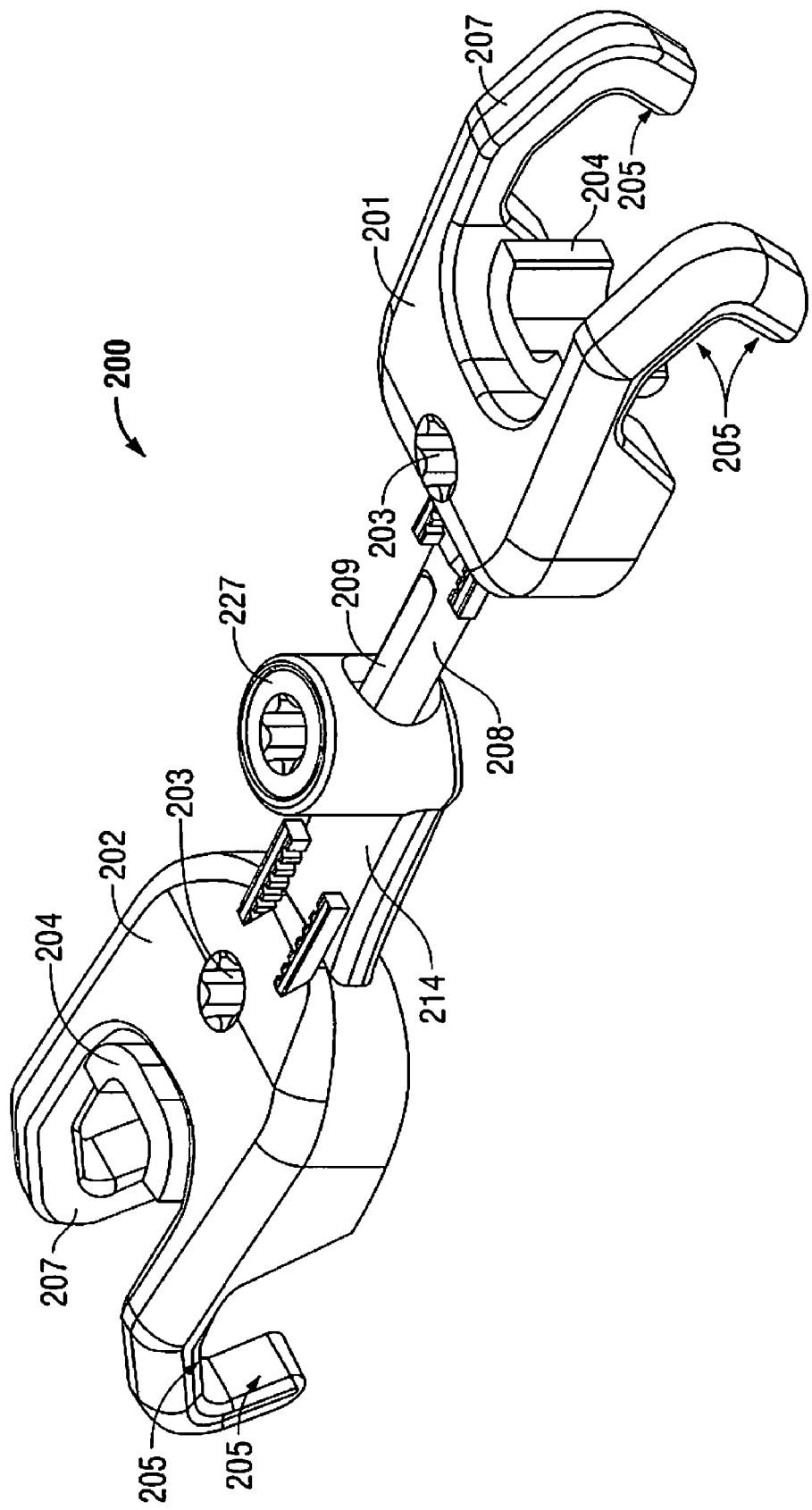
FIG. 12B is a perspective view of the universal connector device of FIG. 12A.
Figure 12C:
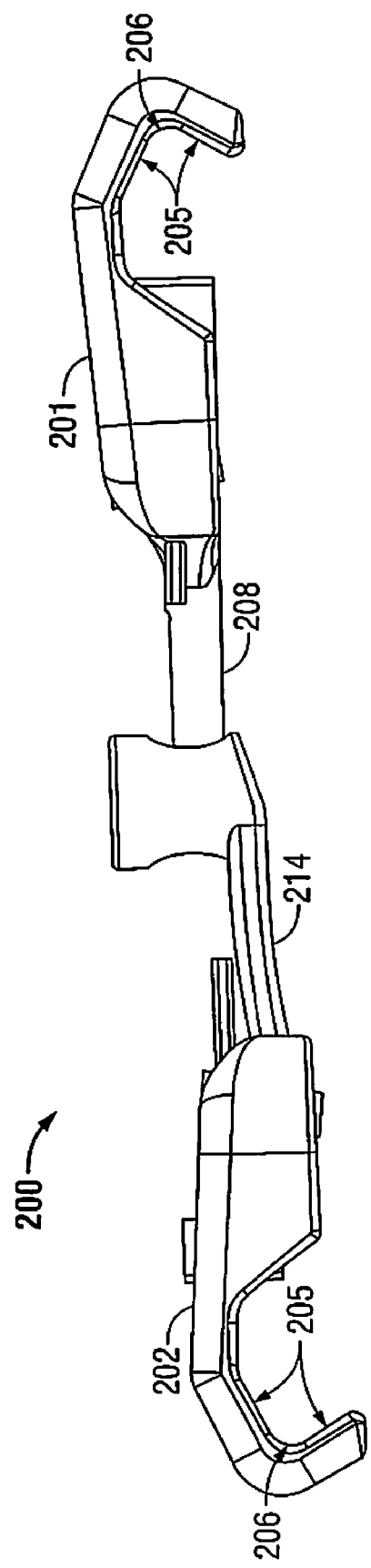
FIG. 12C is a front view of the universal connector device of FIG. 12A.
Figure 15C:
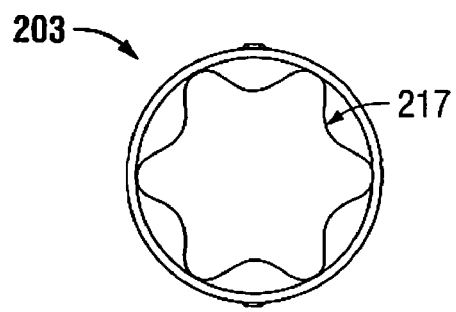
FIG. 15C is a side view of the locking pin of FIG. 15A.
Figure 15C:
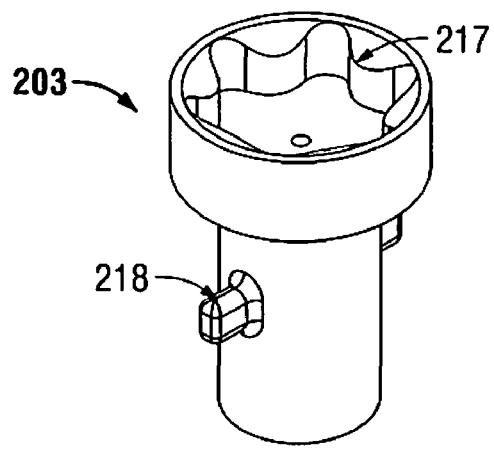
Figure 15C:
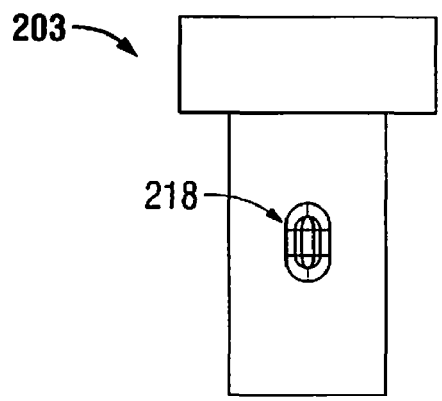
Figure 15D:
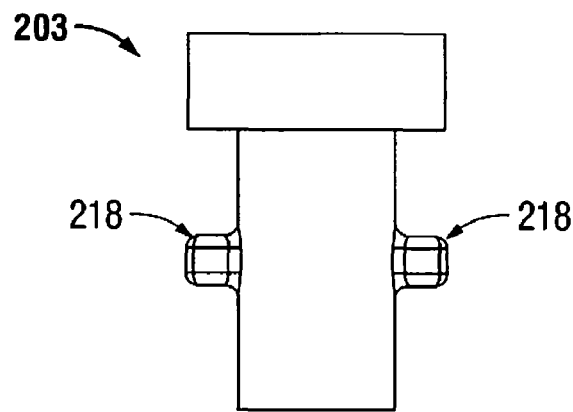
FIG. 15D is front view of the locking pin of FIG. 15A.

FIGS. 12A-12C show an alternate embodiment of the presently disclosed universal transverse connector. This embodiment has been identified in these figures with reference numeral 200. The structure and operation of universal transverse connector 200 is substantially similar to the structure and operation of universal transverse connector 100. For instance, universal transverse connector 200 includes a locking screw 227 interconnecting first and second rod grasping members 201, 202. Universal transverse connector 200, however, secures pedicle screws 108 with a locking mechanism 204 having a locking pin 203, a locking plate 219, and a locking dual rack 220 positioned on each of first and second rod grasping members 201, 202 (see FIGS. 15A and 16B).

With reference to FIGS. 13A-13D, first rod grasping member 201 has a fork-like shape and includes a pair of rod engaging arms 250 defining a space 207 therebetween. Space 207 is dimensioned to accommodate screw bead 138 of pedicle screw 108. Each rod engaging arm 250 of first rod grasping member 201 defines contacting surfaces 205 adapted for engaging spinal fixation rod 109. Contacting surfaces 205 define an acute angle relative to the corresponding longitudinal axes A, B. In one embodiment, contacting surfaces 205 include a filleted portion with a radius 206 dimensioned to accommodate spinal fixation rod 109. This filleted portion reduces stress concentration or stress riser of first rod grasping member 201. Consequently, contacting surfaces 205 have a hook-like or generally C-shaped profile. Radius 206 may vary. For example, radius 206 may match the radius of the smallest commercially available spinal fixation rod 109. First rod grasping member 201 further includes an extension member 208 protruding therefrom. Extension member 208 defines an alignment slot 208 disposed along at least a portion of its length. Alignment slot 208 is configured for slidably receiving an alignment post (not shown) that is substantially similar to alignment post 104 (see FIGS. 6A-6D) of universal transverse connector 100. Like alignment slot 115 of universal transverse connector 100, alignment slot 209 interacts with the alignment post (not shown) to facilitate relative movement between first and second rod grasping members 201, 202.

Figure 13B:
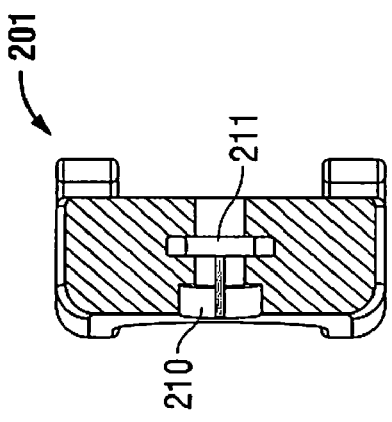
FIG. 13B is a front view of the rod grasping member of FIG. 13A.
Figure 13D:
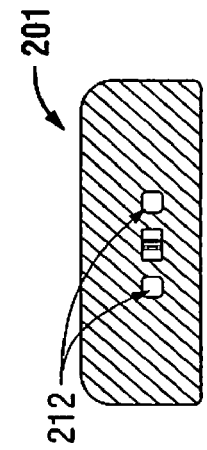
FIG. 13D is a cross-sectional side view of the rod grasping member of FIG. 13A, taken along section line of FIG. 13B.
Figure 13A:
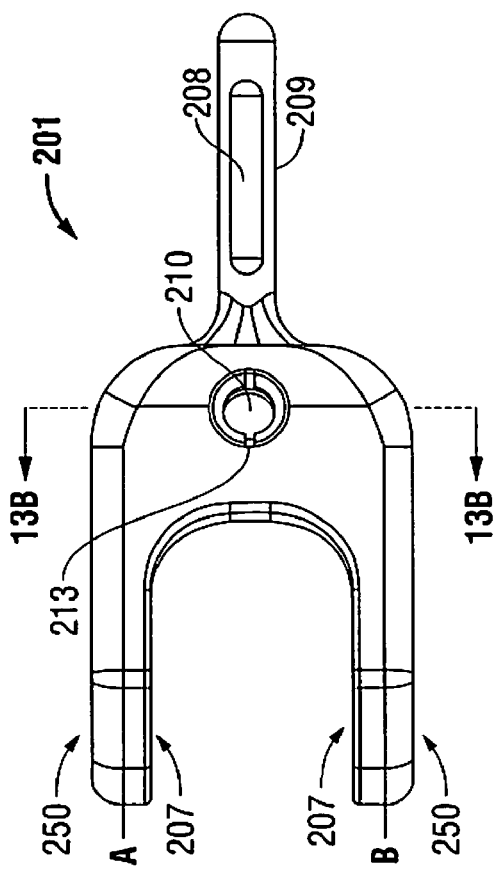
FIG. 13A is a top view of a rod grasping member of the universal connector device of FIG. 12A.
Figure 13C:
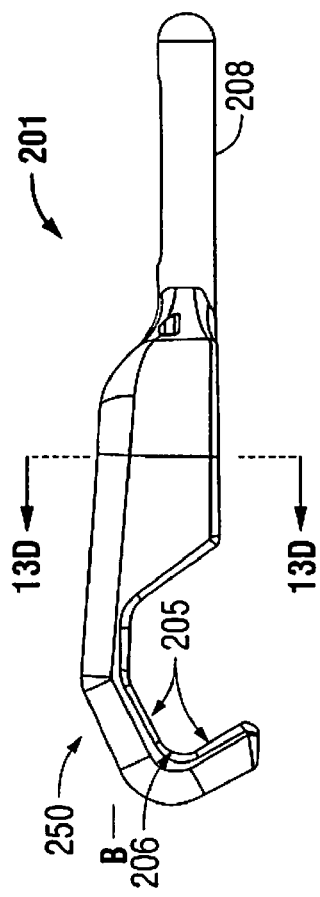
FIG. 13C is a cross-sectional side view of the rod grasping member of FIG. 13A, taken along section line C-C of FIG. 13A.

In addition to extension member 208, first rod grasping member 201 includes a hole 210 adapted to receive locking pin 203 (see FIGS. 15A-15D). As shown in FIGS. 13A and 13C, hole 210 is oriented substantially perpendicular relative to longitudinal axis B and is located at a central portion of first rod grasping member 201 between longitudinal axes A and B. Moreover, hole 210 has an expanded portion 211 configured for slidably receiving locking members or protrusions 218 of locking pin 203 (see FIG. 15B). As seen in FIG. 13C, expanded portion 211 has a cross-section slightly larger than the cross-section of the rest of hole 210. First rod grasping member 201 also defines two openings 212 leading to expanded portion 211 of hole 210. Openings 212 are each adapted for slidably receiving portions of dual rack 220 (see FIG. 16A) and are oriented substantially parallel to longitudinal axes A and B.

Referring to FIGS. 14A-14D, second rod grasping member 202 also includes a hole 210 and two openings 212 leading to an expanded portion (not shown) of hole 210. Hole 210 of second rod grasping member 202 is configured for receiving locking pin 203 (see FIG. 15B) and its expanded portion (not shown) is adapted for slidably receiving locking members or protrusions 218 of locking pin 203 (see FIG. 15B). Besides hole 210 and openings 212, second rod grasping member 202 contains rod engaging arms 250. Each rod engaging arm 250 has contacting surfaces 205 defining an oblique angle relative to longitudinal axes A and B. Contacting surfaces 205 are adapted to engage spinal fixation rod 109 (see FIG. 11A). Furthermore, contacting surfaces 205 of second rod grasping member 202 include a filled portion with a radius 206 dimensioned to accommodate spinal fixation rod 109 (see FIG. 11A). Consequently, contacting surfaces 205 have a hook-like or generally C-shaped profile. Second rod grasping member 202 further includes an extension member 214 protruding therefrom. Unlike first rod grasping member 201, second rod grasping member 202 includes a housing 260 disposed at a proximal end of extension member 214. Housing 260 has a thread 215 formed at an inner surface thereof. Thread 215 is configured for threadably engaging locking screw 227. Housing 260 further includes a portal or opening 216 for receiving extension member 208 of first rod grasping member 201 (see FIG. 13A).

FIGS. 15A-15D show a locking pin 203 of locking assembly 204. As mentioned above, each of first and second rod grasping members 202, 202 has a locking pin 203 disposed in corresponding hole 210 (see FIG. 12A). Locking pin 203 includes a hexalobular drive receiver or socket 217 configured to receive a hexalobular drive and a pair of locking members or protrusions 218 extending therefrom. Locking members 218 are configured for reception within expanded portion 211 of each hole 210. Additionally, locking members 218 are adapted to engage teeth 221 of dual rack 220 (see FIG. 16A). During operation, a user rotates locking pin 203 with a hexalobuar drive to move dual rack 220 toward or away from screw head 138 of pedicle screw 108 (see FIG. 10B).

Figure 16A:
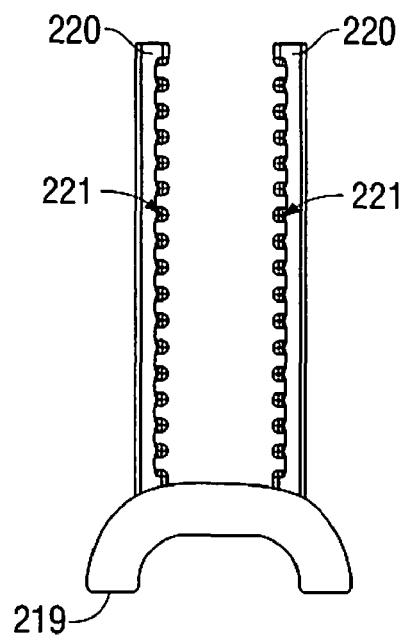
FIG. 16A is a top view of a dual rack of the universal connector device of FIG. 12A.
Figure 16B:
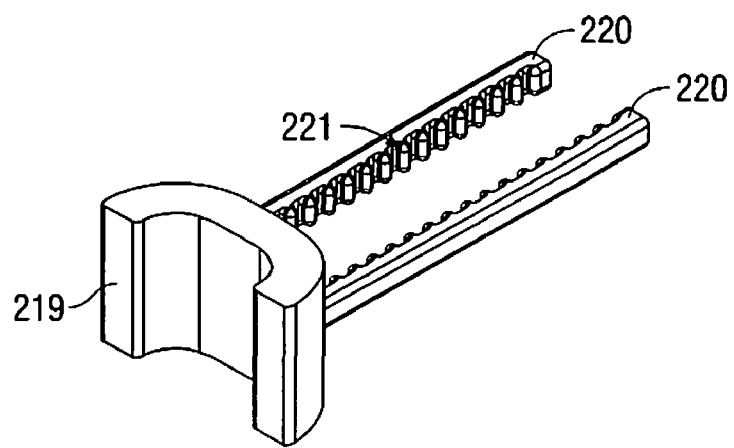
FIG. 16B is a perspective view of the dual rack of FIG. 16A.
Figure 16C:
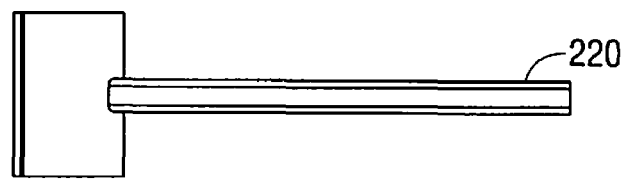
FIG. 16C is a front view of the dual rack of FIG. 16A.

Referring now to FIGS. 16A-16C, each dual rack 220 of locking assembly 204 contains teeth 221 formed on interior portions thereof. Locking plate 219, which is attached to a distal portion of dual rack 220, is configured to engage screw head 138 of pedicle screw 108. As discussed hereinabove, each dual rack 220 is disposed in openings 212 of first and second rod grasping members 201, 202. In operation, dual rack 220 drives locking plate 219 toward or away from screw head 138 of pedicle screw 108 upon rotation of locking pin 203. While the user rotates locking pin 203 (see FIG. 15A), locking members 218 of locking pin 203 engage teeth 221 of dual rack 220. The user can secure first and second rod grasping members 201, 202 to pedicle screws 108 by advancing locking plates 219 toward screw head 138 of pedicle screw 108 until locking plates 219 firmly engages screw heads 138.

In operation, universal transverse connector 200 works in a substantially similar manner as universal transverse connector 100. A user of universal transverse connector 200, however, locks first and second rod grasping members 201, 202 to pedicle screws 108 with locking assembly 204. Locking assembly 204, as discussed above, includes locking pin 203, dual rack 220, and locking plate 219. To secure pedicle screw 108 to universal transverse connector 200, the user initially inserts pedicle screws 108 in vertebral bodies and places spinal fixation rods 109 in saddles 139 of pedicle screws. The user then positions rod engaging arm 250 of universal transverse connector 200 over spinal fixation rods 109. After placing rod engaging arms 250 on top of spinal fixation rods 109, the user rotates locking pin 203 with any suitable driver to move dual rack 220 toward screw head 138 of pedicle screw 108. As locking pin 203 rotates, locking members 218 sequentially engage teeth 221 of dual rack 220, causing dual rack 220 to translate toward screw head 138. Since locking plate 219 is connected to a distal portion of dual rack 220, the translation of dual rack 220 causes the corresponding translation of locking plate 219. While dual racks 220 translates toward screw heads 138, locking plates 219 pushes screw heads 138, along with spinal fixation rods 109, toward contacting surfaces 205. The user has to rotate locking pin 203 until spinal fixation rods 109 firmly engages contacting surfaces 205, thereby securing pedicle screws 108 to universal transverse connector 200.

Figure 17A:
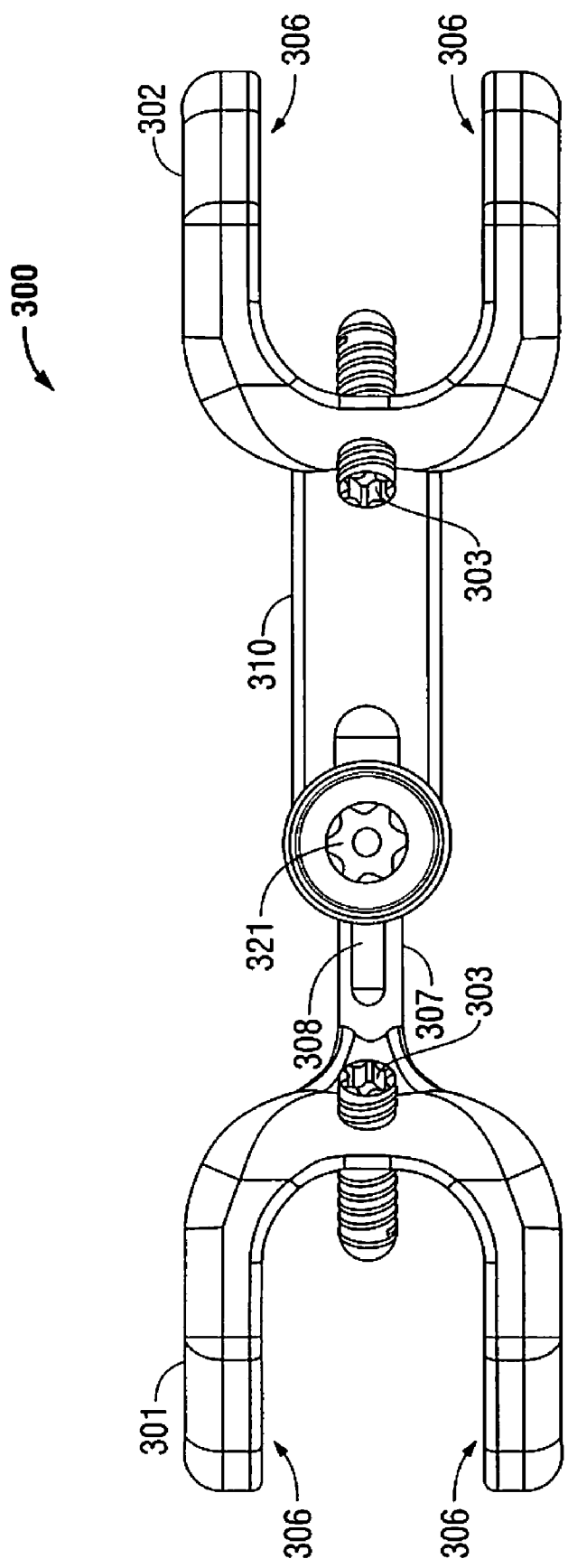
FIG. 17A is a top view of a universal connector device according to a further embodiment of the present disclosure.
Figure 17B:
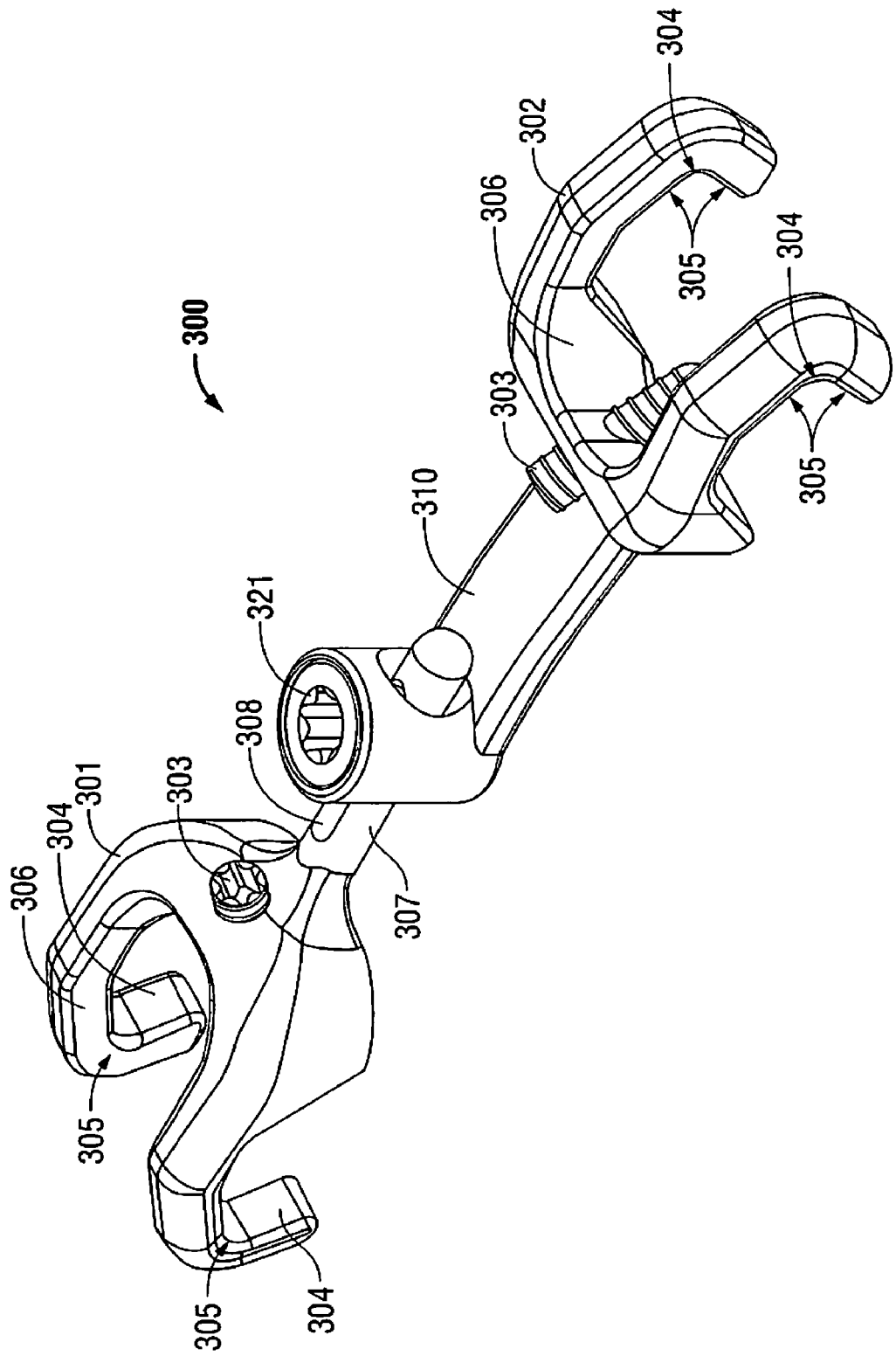
FIG. 17B is perspective view of the universal connector device of FIG. 17A.
Figure 17C:
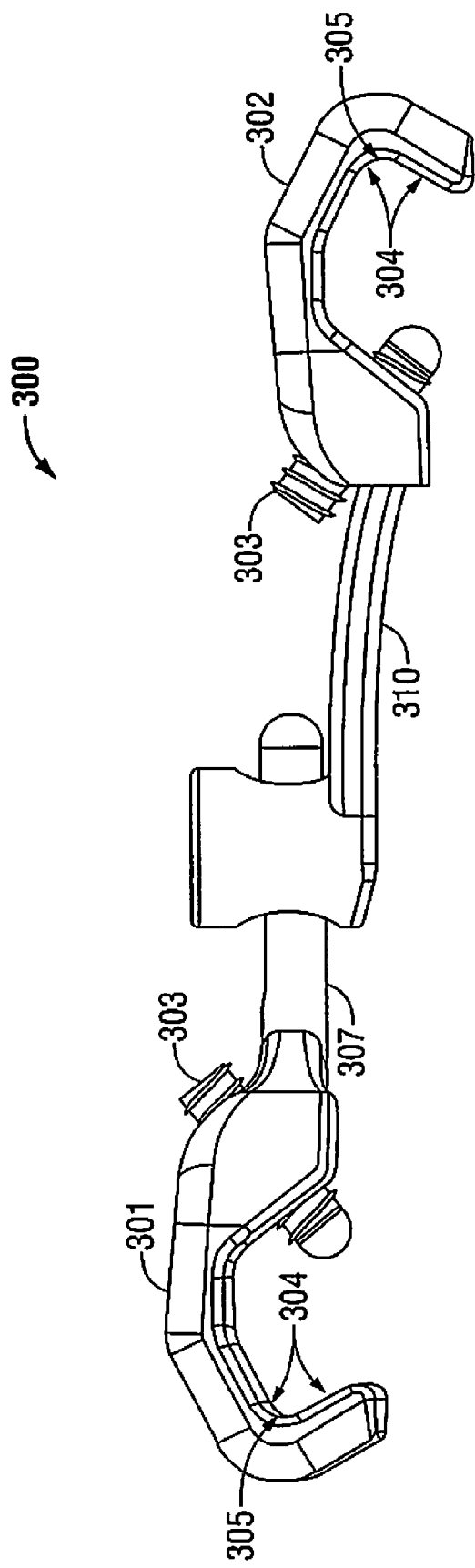
FIG. 17C is a front view of the universal connector device of FIG. 17A.

With reference to FIGS. 17A-17C, the present disclosure shows another embodiment of the universal transverse connector, which has been generally designated with reference numeral 300. The structure and operation of universal transverse connector 300 is substantially similar to the structure and operation of universal transverse connector 100. Like universal transverse connector 100, universal transverse connector 300 includes first and second rod grasping members 301, 302 interconnected by a locking screw 321. Universal transverse connector further includes a slip ring and an alignment post (not shown) for securing and relatively moving first and second rod grasping member 301, 302 relative to each other. The slip ring and alignment post of universal are substantially similar to slip ring 105 and alignment post 104 of universal transverse connector 100. In contrast to universal connector device 100, universal connector device 300 lacks locking plates. However, first and second rod grasping members 301, 301 are substantially similar to rod grasping members 101, 102.

With reference to FIGS. 18A-18D, first rod grasping member 301 includes two rod engaging arms 350 defining a space 306 therebetween. A rod engaging arm 350 defines a longitudinal axis D along at least a portion of a length thereof, and the other rod engaging arm 350 defines a longitudinal axis E along at least a portion of a length thereof. Space 306 is located between longitudinal axes D and E and is configured to accommodate screw head 138 of pedicle screw 108. Each rod engaging arm 350 defines contacting surfaces 304 for engaging spinal fixation rod 109. Contacting surfaces 304 define an acute angle relative to the corresponding longitudinal axes D and E. In addition, contacting surfaces 304 include a filleted portion with a radius 305 dimensioned to at least partially encircle spinal fixation rod 109. Consequently, contacting surfaces 304 have a hook-like or generally C-shaped profile. First rod grasping member 301 additionally includes a threaded hole 309 disposed at a central portion located between longitudinal axes D and E. Threaded hole 309 is configured to receive thread locking pin 303 (see FIG. 20A) and is oriented at an acute angle relative to longitudinal axis D and E. Moreover, first rod grasping member 301 has an extension member 307 protruding therefrom. Extension member 307 defines an alignment slot 308 along at least a portion of a length thereof. Alignment slot 308 is adapted to receive an alignment post (not shown) to facilitate relative movement of first and second rod grasping members 301, 302.

With reference to FIGS. 19A-19D, second rod grasping member 302 includes two rod engaging arms 350 defining a space 306 therebetween. A rod engaging arm 350 defines a longitudinal axis F along at least a portion of a length thereof, and the other rod engaging arm 350 defines a longitudinal axis G along at least a portion of a length thereof. Space 306 is located between longitudinal axes F and G and is configured to accommodate screw head 138 of pedicle screw 108. Each rod engaging arm 350 defines contacting surfaces 304 for engaging spinal fixation rod 109. Contacting surfaces 304 define an acute angle relative to the corresponding longitudinal axes F and G. In addition, contacting surfaces 304 include a filleted portion with a radius 305 dimensioned to at least partially surround spinal fixation rod 109. Consequently, contacting surfaces 304 have a hook-like or generally C-shaped profile. Second rod grasping member 302 additionally includes a threaded hole 309 disposed at a central portion located between longitudinal axes D and E. Threaded hole 309 is configured to receive thread locking pin 303 (see FIG. 20A) and is oriented at an acute angle relative to longitudinal axes F and G. Further, second rod grasping member 302 has an extension member 310 protruding therefrom. Extension member 310 supports a housing 360 in a proximal region thereof. Housing 360 includes threads 311 formed at an inner surface thereof and portal or opening 312 adapted for receiving at extension member 307 of first rod grasping member 301.

Figure 19A:
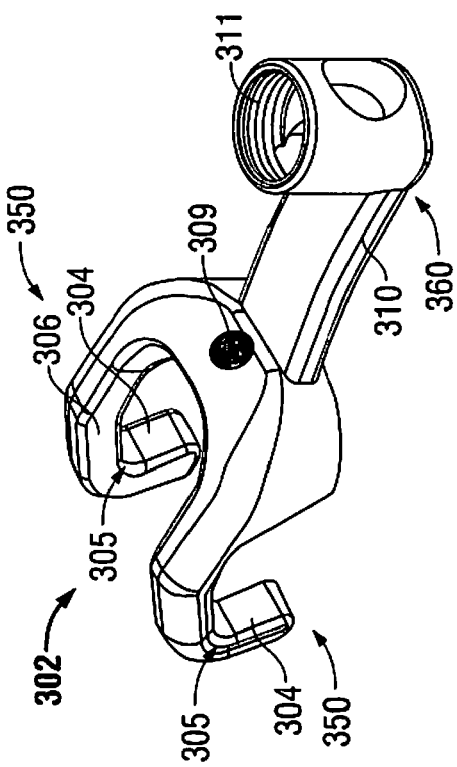
FIG. 19A is a top view of an opposing rod grasping member of the universal connector device of FIG. 17A.
Figure 19B:
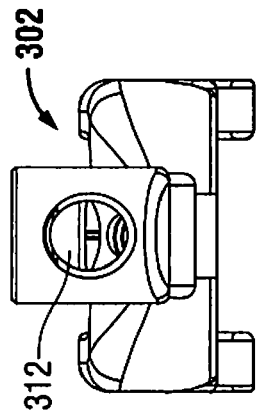
FIG. 19B is a perspective view of the rod grasping member of FIG. 19A.
Figure 19C:
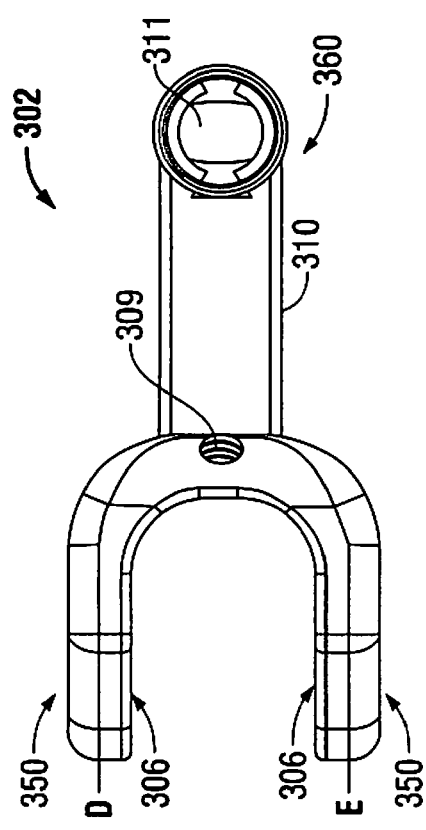
FIG. 19C is a rear view of the rod grasping member of FIG. 19A.
Figure 19D:
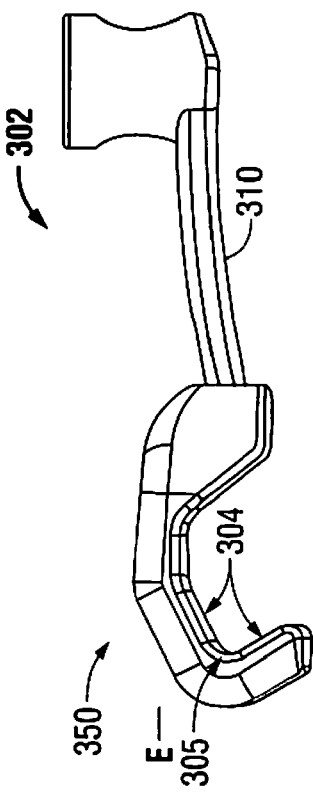
FIG. 19D is a side view of the rod grasping member of FIG. 19A.
Figure 20A:
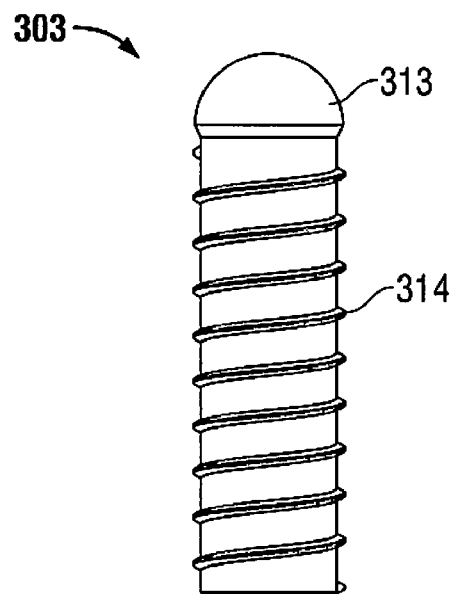
FIG. 20A is a side view of a locking pin of the universal connector device of FIG. 17A.
Figure 20B:
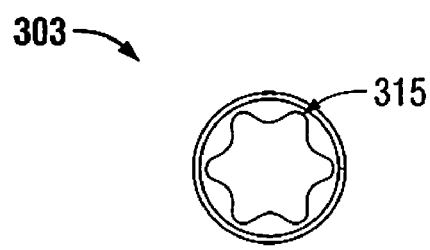
FIG. 20B is a top view of the locking pin of FIG. 20A.
Figure 20C:
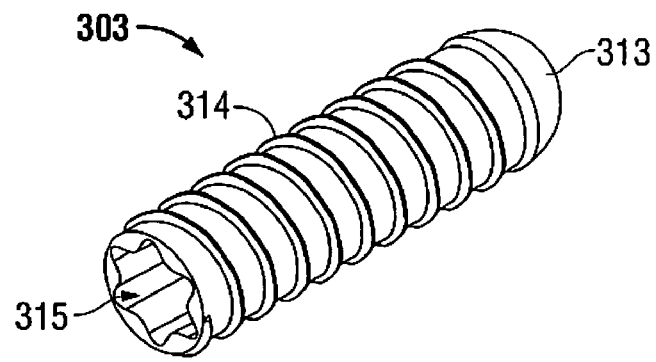
FIG. 20C is a perspective view of the locking pin of FIG. 20A.

Referring to FIGS. 20A-20C, universal transverse connector 300 includes a threaded locking pin 303 disposed in each threaded hole 309 (see FIGS. 17A, 18A, and 19A). Locking pin 303 facilitates attachment of pedicle screws 108 to universal transverse connector 300 and includes a helical thread 314 formed about an outer surface thereof, a blunt distal end 313 configured for engaging screw head 138 of pedicle screw 108 (see FIG. 1C), and a hexalobular drive receiver or socket 315 located at a proximal end. Hexalobular drive receiver 315 is adapted to receive a hexalobular drive or any other suitable driving device capable of rotating locking pin 303.

The operation of universal transverse connector 300 is substantially similar to the operation of universal transverse connector 100. Universal transverse connector 300, however, secures pedicle screw 108 with locking pin 303. A user secures pedicle screws 108 to universal transverse connector 300 by initially inserting pedicle screws 108 into vertebral bodies and placing spinal fixation rods 109 in saddles 139 of pedicle screws 108. Then, the user positions rod engaging arms 250 of universal transverse connector 200 over spinal fixation rods 109. The user subsequently rotates locking pin 303 with any suitable driver to translate locking pin 303 toward screw head 138 through threaded hole 309. As locking pin 309 advances through threaded hole 309 toward screw head 138 of pedicle screw 108 (see FIG. 1C), blunt distal end 313 contacts screw head 138 and pushes screw head 138, along with spinal fixation rods 109, toward contacting surfaces 304. The user keeps rotating locking pin 303 until spinal rods 109 firmly engages contacting surfaces 304, thereby securing pedicle screws 108 to universal transverse connector 300.

Figure 21A:
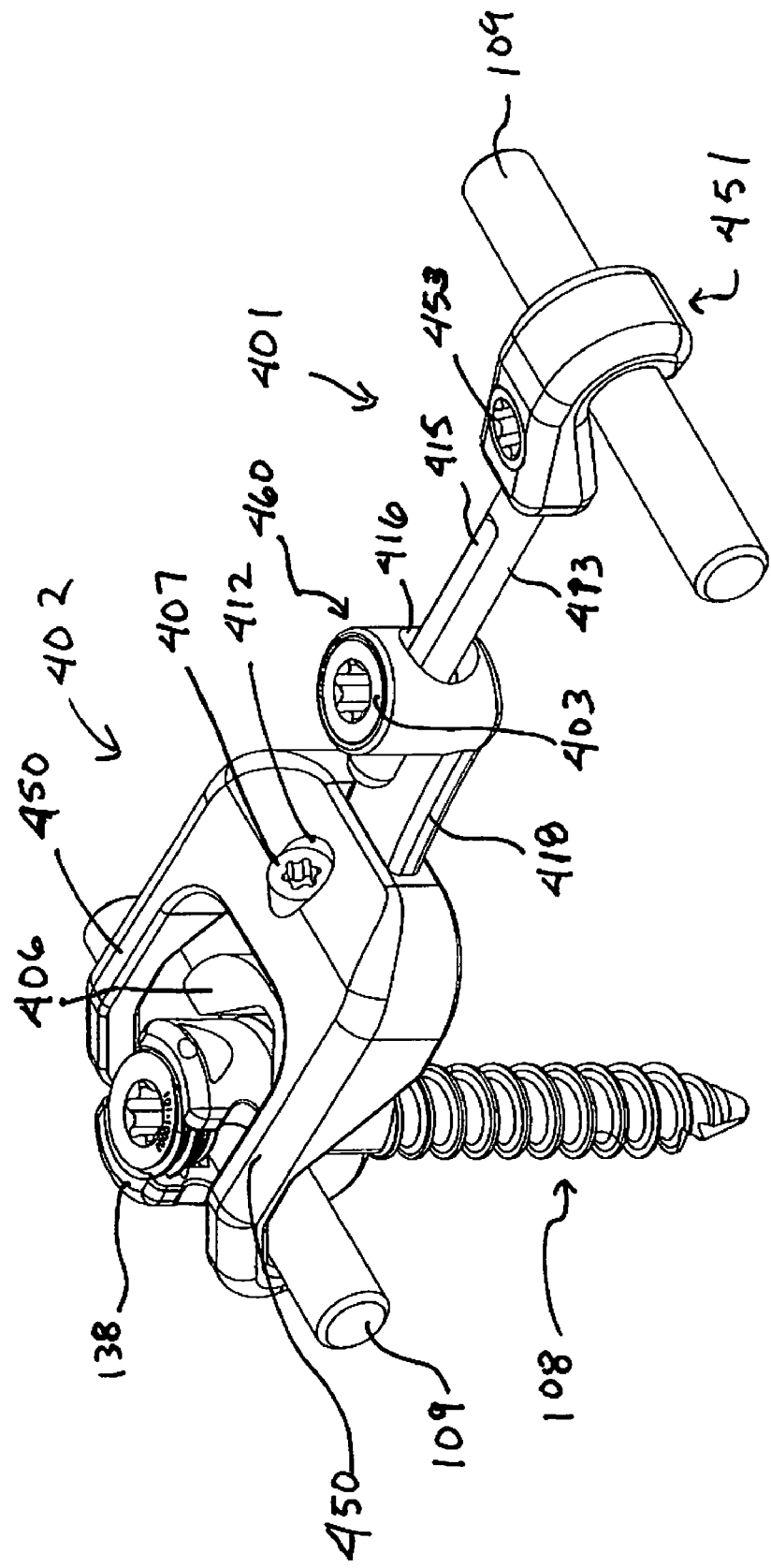
FIG. 21A is a perspective view of a universal connector device according to an embodiment of the present disclosure.
Figure 21B:
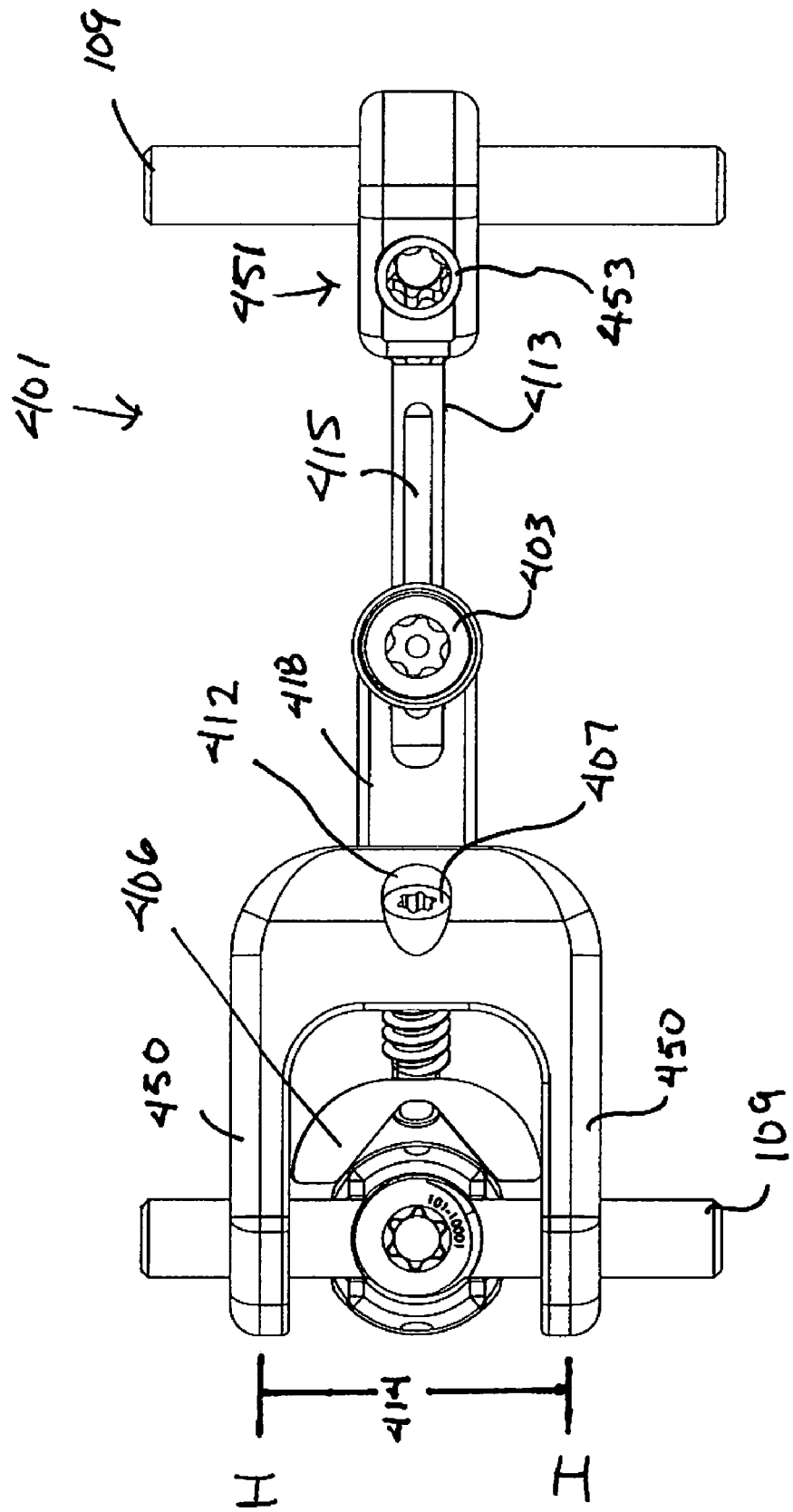
FIG. 21B is a top view of the universal connector device of FIG. 21A.

FIGS. 21A-21C illustrate an alternate embodiment of the presently disclosed universal transverse connector. The depicted universal transverse connector is generally designated with reference numeral 400. Universal transverse connector 400 includes a first grasping member 401 and a second grasping member 402 interconnected by a locking screw 403. Locking screw 403 is substantially similar to locking screw 103 (see FIG. 4A-4C). Second rod grasping member 402 is substantially similar to rod grasping member 102 and contains a plate advancing member 407 operatively coupled to a locking plate 406. Plate advancing member 407 is substantially similar to plate advancing member 107, while locking plate 406 is substantially similar to locking plate 106. Locking plate 406 is adapted to receive and frictionally engage a screw head or tulip 138 of pedicle screw 108. During operation, locking plate 406 moves toward or away from the screw head 138 upon rotation of plate advancing member 407.

The structure and operation of second grasping member 402 is substantially similar to first grasping member 102 of universal transverse connector 100. Like second grasping member 102, second rod grasping member 402 has a fork-like shape and includes a pair of rod engaging arms 450 defining a space 414 therebetween. Space 114 is dimensioned for surrounding the screw head 138 of a pedicle screw 108. Each rod engaging arm 450 defines longitudinal axes H, I extending along at least a portion of its length and includes contacting surfaces 410 for engaging a spinal fixation rod 109, as depicted in FIG. 21C. Contacting surfaces 410 define an acute angle relative to the corresponding longitudinal axes H, I. In one embodiment, contacting surfaces 410 include filleted portion with a radius 411 dimensioned to accommodate spinal fixation rod 109. Consequently, contacting surfaces 410 have a hook-like or generally C-shaped profile. Radius 411 may vary. For example, radius 411 may match the radius of the smallest commercially available spinal fixation rod 109. In addition to rod engaging arms 450, second rod grasping member 402 has a threaded hole 412 located at a center portion thereof. Threaded hole 412 is configured to receive plate advancing member or screw 407 and is oriented at an oblique angle with respect to longitudinal axes H, I. Besides threaded hole 412, second rod grasping member 402 includes an extension member 418 protruding therefrom. Extension member 418 supports a post-receiving housing 460 in a proximal region thereof. Housing 460 includes an inner threaded area (not shown) and a portal or opening 416 adapted for receiving at least a portion of first grasping member 401. Inner threaded area is configured to engage locking screw 403. Though FIGS. 21A-21C show a second grasping member 407, the universal transverse connector 400 may alternatively include second grasping members 202 or 303 of universal transverse connectors 200 or 300.

As mentioned above, universal transverse connector 400 includes a first grasping member 401 operatively coupled to second grasping member 402. In general, first grasping member 401 includes an extension member 413 and a rod engaging arm 451. Extension member 413, which is connected to rod engaging arm 451, defines an alignment slot or recess 415 along its length. Alignment slot 415 is configured for receiving alignment post 104 (see FIG. 6A-6D) to facilitate relative movement between first and second grasping members 401, 402. As seen in FIG. 21B, rod engaging arm 451 may include a screw 453 for aiding in the connection of extension member 413 and rod engaging arm 451. Moreover, rod engaging arm 451 includes a contacting surface 457 defining an opening 455 adapted to receive spinal fixation rod 109. Contacting surface 457 have a hook-like or generally C-shaped profile. The operation of universal connector 400 is substantially similar to the operation of universal connector 100. In contrast to universal transverse connector 100, universal transverse connector secures a spinal fixation rod 109 with rod engaging arm 451. A surgeon secures one spinal fixation rod 109 to universal transverse connector 400 by positioning contacting surface 457 of rod engaging arm 451 around spinal fixation rod 109.

The embodiments of the presently disclosed universal transverse connector may be manufactured from implant grade metallic materials including, but not limited to, titanium and Cobalt chromium alloys, nickel titanium alloys, and stainless steels. The universal transverse connectors disclosed herein may alternatively be made of thermoplastics, composites of plastic and metal, or bioabsorbable materials. Conventional manufacturing techniques as well as nano-manufacturing method may be employed to make the presently disclosed universal transverse connectors.

It will be understood that various modifications may be made to the embodiments of the presently disclosed universal transverse connector. Therefore, the above description should not be construed as limiting, but merely as exemplifications of embodiments. Those skilled in the art will envision other modifications within the scope and spirit of the present disclosure.

What is claimed is:

1. A connection system, comprising:

a first spinal fixation rod;

a second spinal fixation rod;

a first pedicle screw having a first screw head, the first screw head defining a first saddle, wherein the first spinal fixation rod is supported in the first saddle;

a second pedicle screw having a second screw head, the second screw head defining a second saddle, wherein the second spinal fixation rod is supported in the second saddle;

a first grasping member holding the first spinal fixation rod;

a second grasping member holding the second spinal fixation rod, wherein the second grasping member is operatively connected to the first grasping member;

a first rotatable rod disposed in mechanical cooperation with the first grasping member;

a second rotatable rod disposed in mechanical cooperation with the second grasping member;

a first engaging member operatively connected to the first rotatable rod, the first engaging member being adapted to engage the first screw head, wherein the first engaging member is configured to translate upon rotation of the first rotatable rod; and a second engaging member operatively connected to the second rotatable rod, the second engaging member being adapted to engage the second screw head, wherein the second engaging member is configured to translate upon rotation of the second rotatable rod, wherein the first engaging member includes a locking plate configured to advance toward the first screw head upon rotation of the first rotatable rod and the first engaging member includes a dual rack operatively connected to the locking plate, the dual rack being configured to move the locking plate upon rotation of the first rotatable rod.

2. The connection system according to claim 1, wherein the first and second grasping members are configured to move with respect to each other.

3. The connection system according to claim 2, further comprising a locking screw configured for fixing first and second grasping members in place.

4. The connection system according to claim 1, wherein the first rotatable rod includes locking members adapted to engage the dual rack.

5. The connection system according to claim 4, wherein the dual rack includes teeth configured to engage the locking members.

6. The connection system according to claim 1, wherein the first engaging member is an integral part of first rotatable rod.

7. The connection system according to claim 6, wherein the first engaging member is a blunt end of the first rotatable rod.

* * * * *